United States Patent
Bryan et al.

(10) Patent No.: US 7,087,758 B2
(45) Date of Patent: Aug. 8, 2006

(54) QUINOLINE INHIBITORS OF HYAKI AND HYAK3 KINASES

(75) Inventors: Deborah L. Bryan, King of Prussia, PA (US); Joelle L. Burgess, Collegeville, PA (US); James F. Callahan, Collegeville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 205 days.

(21) Appl. No.: 10/474,084

(22) PCT Filed: Apr. 4, 2002

(86) PCT No.: PCT/US02/10657

§ 371 (c)(1),
(2), (4) Date: Oct. 6, 2003

(87) PCT Pub. No.: WO02/081728

PCT Pub. Date: Oct. 17, 2002

(65) Prior Publication Data

US 2005/0043352 A1 Feb. 24, 2005

Related U.S. Application Data

(60) Provisional application No. 60/282,229, filed on Apr. 6, 2001.

(51) Int. Cl.
*A61K 31/47* (2006.01)
*C07D 215/38* (2006.01)
*C07D 215/12* (2006.01)

(52) U.S. Cl. ...................... 546/161; 546/167; 546/159; 514/311; 514/314

(58) Field of Classification Search ................ 514/311, 514/314; 546/161, 167, 159
See application file for complete search history.

(56) References Cited

U.S. PATENT DOCUMENTS

| 5,112,837 A | 5/1992 | Burrows et al. |
| 5,908,930 A | 6/1999 | Dow |
| 6,225,329 B1 | 5/2001 | Richter et al. |
| 6,342,514 B1 | 1/2002 | Petrie et al. |

FOREIGN PATENT DOCUMENTS

| WO | 96/28444 | 9/1996 |
| WO | WO 00/42026 | * 7/2000 |

* cited by examiner

*Primary Examiner*—D. Margaret Seaman
(74) *Attorney, Agent, or Firm*—Kathryn L. Coulter

(57) ABSTRACT

This invention relates to novel quinoline inhibitors of hYAK1 and hYAK3 kinases and pharmaceutically acceptable salts, hydrates or solvates thereof, pharmaceutical compositions thereof, and methods of treatment of diseases in which an excessive amount of either such kinase is a factor.

9 Claims, 3 Drawing Sheets

QUINOLINE INHIBITORS OF HYAK1 AND HYAK3 KINASES

This This application is filed pursuant to 35 U.S.C. § 371 as a United States National Phase Application of International Application No. PCT/US02/10657 filed Apr. 4, 2002, which claims priority from U.S. 60/282,229 filed Apr. 6, 2001.

FIELD OF THE INVENTION

This invention relates to novel quinoline inhibitors of hYAK kinases. Such compounds are particularly useful for treating disease states in which hYAK1 and/or hYAK3 kinases are implicated, especially diseases of the hematopoietic systems, including anemias due to renal insufficiency or to chronic disease, such as autoimmunity or cancer and drug-induced anemias, polycythemia, myelodysplastic syndrome, aplastic anemia and myelosuppression; cytopenia; neurodegeneration; and also for controlling male fertility, especially for the purpose of achieving contraception.

BACKGROUND OF THE INVENTION

The YAK family of serine/threonine protein kinases represent a novel family of dual specificity protein kinases with unique structural, enzymatic, and probably functional features was identified (Becker and Joost (1999) *Prog. Nucl. Acid Res.* 62, 1–17). Four members of this subfamily have been identified by large scale screening of human cDNA libraries using yeast YAK1 sequence, and have been termed h (human)Yak1, 2, 3, and 4. See U.S. Pat. No. 5,972,606 (hYAK1), U.S. Pat. No. 6,001,623 (hYAK2), and U.S. Pat. No. 5,965,420 (hYAK3). In the yeast *S. cerevisiae* YAK1 functions as a negative regulator of cell growth (Garrett, S., Menold, M. M., and Broach, J. (1991) *Mol. Cell. Biol.* 11, 4045–4051). Deletion of the three PKA genes (tpk1, tpk2, and tpk3) in yeast causes cell cycle arrest at $G_1$ while this growth defect is alleviated by removal of the YAK1 gene (Garrett, S., and Broach, J. (1989) *Gene Dev.* 3, 1336–1348). Recent data indicates that yYAK1 expression is controlled by two transcription factors MSN2/4 which are negatively regulated by PKA, thus yYAK1 acts downstream of PKA (Smith, A., Ward, M. P. and Garrett, S. (1998) EMBO J. 17, 3556–3564). While the means by which yYAK1 inhibits cell growth is still not known, overexpression of yYAK1 suppresses cell cycle arrest in late mitotic mutants activity (cdc15, cdc5, dbf2, and tem1) defective in anaphase-promoting complex (APC) (Jaspersen, S. L. Charles, J. F., Tinker-Kulberg, R. L., and Morgan, D. O. (1998) *Mol. Biol. of the Cell.* 9, 2803–2817). Recent work in Dictyostelium has uncovered a yYAK1 homolog which is required for the transition from growth to development giving support to the involvement of this family of kinases in cell growth (Souza, G. M., Lu, S. and Kuspa, A. (1998) Development 125, 2291–2302).

Human multi-tissue northern blot analysis indicated that hYAK1 is expressed as a ~10 kb, 7.0 kb and 2.6 kb transcript. The multiple transcripts are not due to cross-hybridization with other YAK family members since the 3'UTR was used as a probe and the closest known homolog to hYAK1, hYAK3, shares only 62% identity with hYAK1 at the nucleotide level. In addition, alternatively spliced forms were identified within the 3' UTR indicating that the multiple transcripts are due to alternative splicing within the untranslated regions. The most abundant transcripts were found in skeletal muscle and heart followed by pancreas, placenta, brain and lung. Multiple transcripts of the same apparent size were also seen in various osteoblastoid (HOS, MG63, Hob), stromal (TF274) and chondrocyte (C20A4) cell lines confirming that hYAK1 is expressed in these tissues. In situ hybridization studies were done using $^{35}$S-labeled riboprobes on cryosections of human bone and giant cell tumor. Autoradiographic development times were extended (3 weeks) to compensate for the generally low level of mRNA expression of hYAK1 kinase observed in the initial studies. In human fetal bone and osteophyte, various osteoblast populations were strongly (3+) positive for the expression of hYAK1 kinase mRNA. Many other cell types including bone marrow and chondrocytes had varying levels of expression (1–2+). In giant cell tumor, the diverse population of cell types including stromal, osteoblast precursors and osteoclasts were all positive (2+) for hYAK1 kinase expression.

Several lines of evidence from our research findings strongly suggest that hYAK1, like YAK1 in yeast functions as a negative regulator of cell cycle progression. Overexpression of wild type hYAK1 in cells causes a delay in exit from G2/M phase. Conversely, hYAK1 kinase inhibitors selectively cause an accumulation of S phase cells. This in turn causes changes in the expression of bone specific markers and products from chondrocytes. Specifically, YAK1 inhibitors are expected to increase bone formation and/or to be chrondroprotective.

Northern analysis was carried out to determine the distribution of hYAK3 mRNA in human tissues. Membranes containing mRNA from multiple human tissues (Clontech #7760-1, #7759-1, and #7768-1) were hybridized to an hYAK3 probe and washed under high stringency conditions as directed. Hybridized mRNA was visualized by exposing the membranes to X-ray film. One major transcript at ~2.5 kb was present in testis, and transcripts of 2.5, 8 and 10 kb were present in bone and fetal liver. The transcripts were not visible in any other tissues; however, dot blot analysis using a Human Master blot (Clontech #7770-1) indicated that hYAK3 is expressed in other tissues including skeletal muscle.

Investigations with primary cells and hematopoietic cell lines from both human and mouse indicate that cells of the erythroid lineage may predominantly account for the elevated hYAK3 expression. These data suggest that hYAK3 may have lineage-specific function. In cell lines, hYAK3 is present at higher levels in cells with an erythroid phenotype than other hematopoietic lineages, including myeloid, monocytic and lymphoid cell lines. This profile is completely distinct from hYAK1 which has been observed only at low constitutive levels in hematopoietic cells and tissues. EPO-treatment of human bone marrow in vitro leads to induction and sustained expression of hYAK3 message and hYAK3 protein. Splenocytes from mice made anemic by phenylhydrazine treatment become enriched in erythroid progenitors and exhibit increased expression of hYAK3. Increases in both message and protein accompany induction of erythroid differentiation in UT7-EPO cells.

In yeast, yYAK is a negative regulator of growth via the cell cycle. Consequently, we would anticipate that hYAK3 participates in cell cycle control, and/or commitment to differentiation. We predict that an antagonist of hYAK3 would have a positive effect on cell growth. Our data indicates that it also may be involved in terminal differentiation and growth arrest in hematopoietic cells, especially in the erythroid lineage. Therefore compounds which antagonize YAK3 function or activity may be therapeutically useful in treating conditions of hematopoietic cellular deficiency, such as anemias, including anemias due to renal insufficiency or to chronic disease, such as autoimmunity or cancer, neutropenia, cytopenia, drug-induced anemias, polycythemia, cancer and myelosuppression.

It now has been discovered that a certain novel quinoline inhibitors of hYAK1 and/or hYAK3 kinases are useful for treating diseases of the erythroid and hematopoietic systems, including anemias due to renal insufficiency or to chronic disease, such as autoimmunity or cancer and drug-induced anemias, polycythemia, myelodysplastic syndrome, aplastic anemia and myelosuppression; cytopenia; neurodegeneration; and are also useful for controlling male fertility, especially for the purpose of achieving contraception.

SUMMARY OF THE INVENTION

An object of the present invention is to provide novel quinoline inhibitors of hYAK1 and/or hYAK3 kinases. The compounds of the present invention are useful for treating diseases which may be therapeutically modified by altering the activity of such kinases.

Accordingly, in the first aspect, this invention provides a compound, according to Formula I.

In another aspect, this invention provides a pharmaceutical composition comprising a compound according to Formula I and a pharmaceutically acceptable carrier.

In yet another aspect, this invention provides a method of treating diseases in which the disease pathology may be therapeutically modified by inhibiting hYAK1 and/or hYAK3 kinases with compounds of Formula II, which include the compounds of Formula I. In particular, the method includes treating diseases by inhibiting the activity of such kinases.

In still another aspect, the compounds of this invention are especially useful for treating diseases of the erythroid and hematopoietic systems, including anemias due to renal insufficiency or to chronic disease, such as autoimmunity or cancer and drug-induced anemias, polycythemia, myelodysplastic syndrome, aplastic anemia and myelosuppression; cytopenia; and are also useful for controlling male fertility, especially for the purpose of contraception.

DETAILED DESCRIPTION OF THE INVENTION

Figure 1:
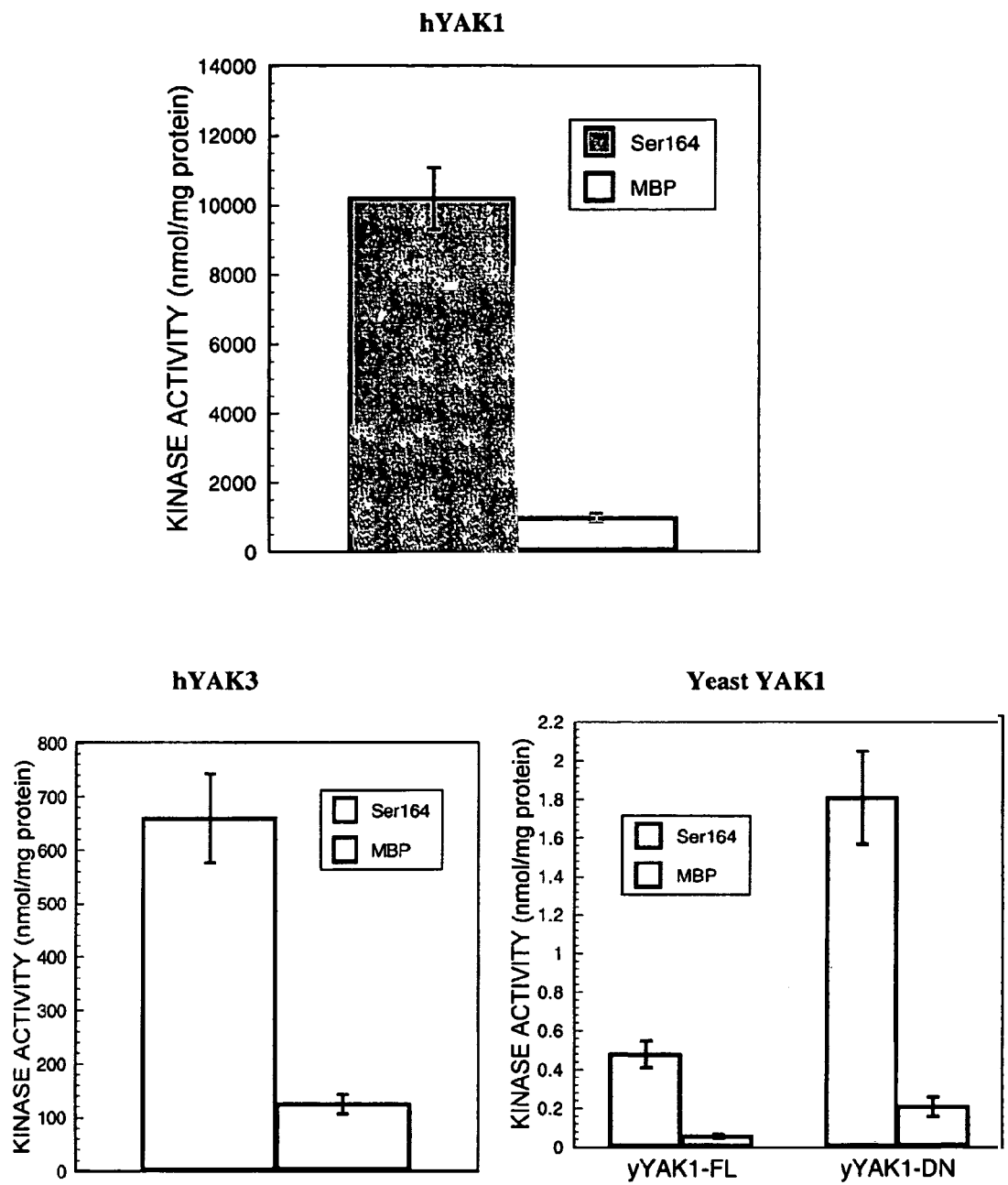
FIG. 1 shows the activity of hYAK1, hYAK3, and yeast YAK1 against MBP and the Ser164 peptide. 5 ng purified hYAK1 and 100 ng purified hYAK3 were used per assay. Anti-HA mAb immune complex kinase assay was performed on 100 ug protein from crude extracts of yeast cells expressing either FL or DN yeast YAK1. Concentration of ATP was 100 uM, Ser164 was used at 0.5 mM, and MBP was at 10 ug/reaction (18.5 uM).

The present invention provides a compound of Formula (I):

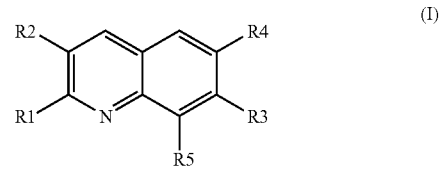

wherein:
R$_1$ is selected from the group consisting of: —NH—C$_{1-6}$alkyl, —NH—C$_{3-7}$ cycloalkyl, —NH—C$_{3-7}$ cycloheteroalkyl, —NH-aryl, —NH-Het, —O—C$_{1-6}$alkyl, —O—C$_{3-7}$ cycloalkyl, —O—C$_{3-7}$ cycloheteroalkyl, —O-aryl, —O-Het, —S—C$_{1-6}$ alkyl, —S—C$_{3-7}$ cycloalkyl, —S—C$_{3-7}$ cycloheteroalkyl, —S-aryl, —S-Het, —C$_{3-7}$ cycloalkyl and —C$_{3-7}$ cycloheteroalkyl;

R$_2$ is selected from the group consisting of: —CO$_2$H, —CONH$_2$, —CHNOH, —CO$_2$R', —CH$_2$OH, —CHO, —CONHR'', —CONHCOR'', and —CONHSO$_2$R'';

R$_3$ is selected from the group consisting of: —H, —OH, —C$_{1-6}$alkyl, —C$_{3-7}$ cycloalkyl, aryl, Het, —O—C$_{1-6}$ alkyl, —O—C$_{3-7}$ cycloalkyl, —O-aryl, —O-Het, —S—C$_{1-6}$alkyl, —S—C$_{3-7}$ cycloalkyl, —S-aryl, —S-Het, —NH—C$_{1-6}$alkyl, —NH—C$_{3-7}$ cycloalkyl, —NH-aryl, —NH-Het and halogen;

R$_4$ is selected from the group consisting of: —H, —C$_{1-6}$ alkyl, —C$_{3-7}$ cycloalkyl, aryl, Het, —O—C$_{1-6}$alkyl, —O—C$_{3-7}$ cycloalkyl, —O-aryl, —O-Het, —S—C$_{1-6}$ alkyl, —S—C$_{3-7}$ cycloalkyl, —S-aryl, —S-Het, —NH—C$_{1-6}$alkyl, —NH—C$_{3-7}$ cycloalkyl, —NH-aryl, —NH-Het and halogen;

R$_3$ and R$_4$ can form a 5 to 7 membered ring comprising 0–3 heteroatoms independently selected from the group consisting of: O, N, and S;

R$_5$ is selected from the group —H and halogen;

R' is selected from the group consisting of: —C$_{1-6}$alkyl, —C$_{3-7}$cycloalkyl, and —C$_{3-7}$cycloheteroalkyl; and R'' is selected from the group consisting of: —C$_{1-6}$alkyl, —C$_{3-7}$cycloalkyl, —C$_{3-7}$cycloheteroalkyl, aryl, and Het;

or a pharmaceutically acceptable salt, hydrate or solvate thereof.

Preferred are compounds of Formula I wherein:
R$_1$ is preferably selected from the group consisting of: —NH—C$_{1-6}$alkyl, —NH-aryl, —NH-Het, —O-aryl, —O-Het, —S-aryl, —S-Het, and —C$_{3-7}$ cycloheteroalkyl,;

R$_2$ is preferably selected from the group consisting of: —CO$_2$H, —CONH$_2$, and —CO$_2$R';

R$_3$ is preferably selected from the group consisting of: —H, —C$_{1-6}$alkyl, —O—C$_{1-6}$alkyl, —S—C$_{1-6}$alkyl, and halogen; and R$_4$ is preferably selected from the group consisting of: —H, —O—C$_{1-6}$alkyl, —S—C$_{1-6}$alkyl, and halogen.

When R$_2$ is —CO$_2$R', R' is preferably selected from the group consisting of: —C$_{1-6}$alkyl, and —C$_{3-7}$cycloalkyl.

More preferred are compounds of Formula I wherein:
- $R_1$ is more preferably selected from the group consisting of: —NH—$C_{1-6}$alkyl, —NH—aryl, —NH-Het, and —$C_{3-7}$cycloheteroalkyl,;
- $R_2$ is more preferably selected from the group consisting of: —$CO_2H$ and —$CONH_2$;
- $R_3$ is more preferably selected from the group consisting of: —H, —$C_{1-6}$alkyl, —O—$C_{1-6}$alkyl, —S—$C_{1-6}$alkyl, and halogen; and
- $R_4$ is more preferably selected from the group consisting of: —H and halogen, even more preferably $R_4$ is H; and
- $R_5$ is more preferably —H.

Even more preferred are compounds of Formula I wherein, in $R_1$:
- —NH-aryl is most preferably selected from the group consisting of: methylphenylamino, especially 3-methylphenylamino (also known as m-tolylamino); ethylphenylamino, especially 3-ethylphenylamino, 4-ethylphenylamino; cyclohexylphenylamino, especially 4-cyclohexylphenylamino; dimethylphenylamino, especially 3,4-dimethylphenylamino; chlorophenylamino, especially 2-chlorophenylamino, 3-chlorophenylamino, 4-chlorophenylamino; fluorophenylamino, especially 2-fluorophenylamino, 4-fluorophenylamino; iodophenylamino, especially 4-iodophenylamino; chlorobenzylamino, especially 4-chlorobenzylamino; morpholinophenylamino, especially 4-morpholin-4-yl-phenylamino; cyanophenylamino, especially 3-cyanophenylamino, 4-cyanophenylamino; ethoxyphenylamino, especially 4-ethoxyphenylamino; dimethoxyphenylamino, especially 3,4-dimethoxyphenylamino, phenoxyphenylamino, especially 4-phenoxyphenylamino; and fluoro-ethoxyphenylamino, especially 2-fluoro-3-ethoxyphenylamino;
- —NH-Het is most preferably selected from the group consisting of: quinolinylamino, especially quinolin-3-ylamino, quinolin-5-ylamino, quinolin-8-ylamino; pyridinylamino, especially pyridin-3-ylamino; and methoxy-pyridinylamino, especially 6-methoxy-pyridin-3-ylamino;
- —$C_{3-7}$ cycloheteroalkyl is most preferably piperidino, especially N-piperidino; and
- —NH—$C_{1-6}$alkyl is preferably propylamino, especially 2-propylamino; and in $R_3$:
- —$C_{1-6}$alkyl is most preferably selected from the group consisting of: methyl and ethyl;
- —O—$C_{1-6}$alkyl is most preferably methoxy;
- —S—$C_{1-6}$alkyl is most preferably methylsulfanyl; and halogen is most preferably chloro.

Especially preferred compounds of the present invention are:
2-(3-Chloro-phenylamino)-7-methoxy-quinoline-3-carboxylic acid;
7-Chloro-2-(3-chloro-phenylamino)-quinoline-3-carboxylic acid; 2-(3-Chloro-phenylamino)-7-methylsulfanyl-quinoline-3-carboxylic acid;
2-(4-Chloro-phenylamino)-7-methoxy-quinoline-3-carboxylic acid;
2-(3-Chloro-phenylamino)-7-methoxy-quinoline-3-carboxylic acid amide
2-(4-Chloro-benzylamino)-7-methoxy-quinoline-3-carboxylic acid;
7-Methoxy-2-(4-phenoxy-phenylamino)-quinoline-3-carboxylic acid
7-Methoxy-2-(4-morpholin-4-yl-phenylamino)-quinoline-3-carboxylic acid;
2-(3-Chloro-phenylamino)-quinoline-3-carboxylic acid;
2-(3-Chloro-phenylamino)-7-methyl-quinoline-3-carboxylic acid;
2-(3-Chloro-phenylamino)-6-methoxy-quinoline-3-carboxylic acid;
2-(3-Chloro-phenylamino)-7-ethyl-quinoline-3-carboxylic acid;
2-(3-Cyano-phenylamino)-7-methoxy-quinoline-3-carboxylic acid;
7-Methoxy-2-m-tolylamino-quinoline-3-carboxylic acid;
2-(4-Ethoxy-phenylamino)-7-methoxy-quinoline-3-carboxylic acid;
2-(4-Cyclohexyl-phenylamino)-7-methoxy-quinoline-3-carboxylic acid;
2-(4-Fluoro-phenylamino)-7-methoxy-quinoline-3-carboxylic acid;
2-(2-Chloro-phenylamino)-7-methoxy-quinoline-3-carboxylic acid;
2-(4-Ethyl-phenylamino)-7-methoxy-quinoline-3-carboxylic acid;
2-(3-Ethyl-phenylamino)-7-methoxy-quinoline-3-carboxylic acid;
2-(4-Cyano-phenylamino)-7-methoxy-quinoline-3-carboxylic acid;
7-Methoxy-2-(quinolin-3-ylamino)-quinoline-3-carboxylic acid;
2-(4-Iodo-phenylamino)-7-methoxy-quinoline-3-carboxylic acid;
7-Methoxy-2-(pyridin-3-ylamino)-quinoline-3-carboxylic acid;
7-Methoxy-2-(6-methoxy-pyridin-3-ylamino)-quinoline-3-carboxylic acid;
7-Methoxy-2-(quinolin-8-ylamino)-quinoline-3-carboxylic acid;
7-Methoxy-2-(quinolin-5-ylamino)-quinoline-3-carboxylic acid;
2-(3,4-Dimethoxy-phenylamino)-7-methoxy-quinoline-3-carboxylic acid;
2-(3,4-Dimethyl-phenylamino)-7-methoxy-quinoline-3-carboxylic acid;
2-(2-Fluoro-phenylamino)-7-methoxy-quinoline-3-carboxylic acid;,
2-(4-Ethoxy-2-fluoro-phenylamino)-7-methoxy-quinoline-3-carboxylic acid;
7-Methoxy-2-piperidin-1-yl-quinoline-3-carboxylic acid; and 7-Methoxy-2-propylamino-quinoline-3-carboxylic acid.

The compounds in the paragraph above may also be named as follows, in the same order as above:
2-(3-chloroanilino)-3-carboxy-7-methoxy-quinoline;
2-(3-chloroanilino)-3-carboxy-7-chloro-quinoline; 2-(3-chloroanilino)-3-carboxy-7-methylthio-quinoline;
2-(4-chloroanilino)-3-carboxy-7-methoxy-quinoline;
2-(3-chloroanilino)-3-carboxamido-7-methoxy-quinoline;
2-(4-chlorobenzylamino)-3-carboxy-7-methoxy-quinoline;
2-(4-phenoxyanilino)-3-carboxy-7-methoxy-quinoline;
2-(4-morpholinanilino)-3-carboxy-7-methoxy-quinoline;
2-(3-chloroanilino)-3-carboxy-quinoline;
2-(3-chloroanilino)-3-carboxy-7-methyl-quinoline;
2-(3-chloroanilino)-3-carboxy-6-methoxy-quinoline;
2-(3-chloroanilino)-3-carboxy-7-ethyl-quinoline;
2-(3-cyanoanilino)-3-carboxy-7-methoxy-quinoline;
2-(3-methylanilino)-3-carboxy-7-methoxy-quinoline;
2-(4-ethoxyanilino)-3-carboxy-7-methoxy-quinoline;
2-(4-cyclohexylanilino)-3-carboxy-7-methoxy-quinoline;

2-(4-fluoroanilino)-3-carboxy-7-methoxy-quinoline;
2-(2-chloroanilino)-3-carboxy-7-methoxy-quinoline;
2-(4-ethylanilino)-3-carboxy-7-methoxy-quinoline;
2-(3-ethylanilino)-3-carboxy-7-methoxy-quinoline;
2-(4-cyanoanilino)-3-carboxy-7-methoxy-quinoline;
2-(3-aminoquinolino)-3-carboxy-7-methoxy-quinoline;
2-(4-iodoanilino)-3-carboxy-7-methoxy-quinoline;
2-(3-aminopyridino)-3-carboxy-7-methoxy-quinoline;
2-(5-amino-2-methoxypyridino)-3-carboxy-7-methoxy-quinoline;
2-(8-aminoquinolino)-3-carboxy-7-methoxy-quinoline;
2-(5-aminoquinolino)-3-carboxy-7-methoxy-quinoline;
2-(3,4-dimethoxyanilino)-3-carboxy-7-methoxy-quinoline;
2-(3,4-dimethylanilino)-3-carboxy-7-methoxy-quinoline;
2-(2-fluoroanilino)-3-carboxy-7-methoxy-quinoline;
2-(2-fluoro-3-ethoxyanilino)-3-carboxy-7-methoxy-quinoline;
2-piperidino-3-carboxy-7-methoxy-quinoline; and 2-propylamino-3-carboxy-7-methoxy-quinoline.

More Especially Preferred Compounds of the Present Invention are:
2-(3-Chloro-phenylamino)-7-methoxy-quinoline-3-carboxylic acid;
7-Chloro-2-(3-chloro-phenylamino)-quinoline-3-carboxylic acid; 2-(3-Chloro-phenylamino)-7-methylsulfanyl-quinoline-3-carboxylic acid;
2-(4-Chloro-phenylamino)-7-methoxy-quinoline-3-carboxylic acid;
2-(4-Chloro-benzylamino)-7-methoxy-quinoline-3-carboxylic acid;
7-Methoxy-2-(4-phenoxy-phenylamino)-quinoline-3-carboxylic acid;
2-(3-Cyano-phenylamino)-7-methoxy-quinoline-3-carboxylic acid;
7-Methoxy-2-m-tolylamino-quinoline-3-carboxylic acid;
2-(4-Ethoxy-phenylamino)-7-methoxy-quinoline-3-carboxylic acid
2-(4-Cyclohexyl-phenylamino)-7-methoxy-quinoline-3-carboxylic acid;
2-(4-Fluoro-phenylamino)-7-methoxy-quinoline-3-carboxylic acid;
2-(2-Chloro-phenylamino)-7-methoxy-quinoline-3-carboxylic acid;
2-(4-Ethyl-phenylamino)-7-methoxy-quinoline-3-carboxylic acid;
2-(3-Ethyl-phenylamino)-7-methoxy-quinoline-3-carboxylic acid;
2-(4-Cyano-phenylamino)-7-methoxy-quinoline-3-carboxylic acid;
7-Methoxy-2-(quinolin-3-ylamino)-quinoline-3-carboxylic acid;
2-(4-Iodo-phenylamino)-7-methoxy-quinoline-3-carboxylic acid;
7-Methoxy-2-(6-methoxy-pyridin-3-ylamino)-quinoline-3-carboxylic acid;
7-Methoxy-2-(quinolin-8-ylamino)-quinoline-3-carboxylic acid;
7-Methoxy-2-(quinolin-5-ylamino)-quinoline-3-carboxylic acid;
2-(3,4-Dimethoxy-phenylamino)-7-methoxy-quinoline-3-carboxylic acid;
2-(2-Fluoro-phenylamino)-7-methoxy-quinoline-3-carboxylic acid; and
2-(4-Ethoxy-2-fluoro-phenylamino)-7-methoxy-quinoline-3-carboxylic acid.

Most Especially Preferred Compounds of the Present Invention are:
2-(3-Chloro-phenylamino)-7-methoxy-quinoline-3-carboxylic acid;
2-(3-Chloro-phenylamino)-7-methylsulfanyl-quinoline-3-carboxylic acid;
2-(4-Chloro-phenylamino)-7-methoxy-quinoline-3-carboxylic acid;
2-(3-Cyano-phenylamino)-7-methoxy-quinoline-3-carboxylic acid;
7-Methoxy-2-m-tolylamino-quinoline-3-carboxylic acid;
2-(4-Ethoxy-phenylamino)-7-methoxy-quinoline-3-carboxylic acid;
2-(4Fluoro-phenylamino)-7-methoxy-quinoline-3-carboxylic acid;
2-(2-Chloro-phenylamino)-7-methoxy-quinoline-3-carboxylic acid;
2-(4-Ethyl-phenylamino)-7-methoxy-quinoline-3-carboxylic acid;
2-(3-Ethyl-phenylamino)-7-methoxy-quinoline-3-carboxylic acid;
2-(4Cyano-phenylamino)-7-methoxy-quinoline-3-carboxylic acid;
2-(4-Iodo-phenylamino)-7-methoxy-quinoline-3-carboxylic acid;
7-Methoxy-2-(quinolin-8-ylamino)-quinoline-3-carboxylic acid;
7-Methoxy-2-(quinolin-5-ylamino)-quinoline-3-carboxylic acid;
2-(2-Fluoro-phenylamino)-7-methoxy-quinoline-3-carboxylic acid; and
2-(4-Ethoxy-2-fluoro-phenylamino)-7-methoxy-quinoline-3-carboxylic acid.

The present invention includes all hydrates, solvates, complexes, polymorphs and prodrugs of the compound of Formula (I). Prodrugs are any covalently bonded compounds which release the active parent drug according to Formula (I) in vivo. Prodrugs of the compound of the present invention include ketone derivatives, specifically ketals or hemiketals.

All forms of isomers resulting from the presence of a chiral center in the inventive compound, including enantiomers and diastereomers, are intended to be covered herein. The inventive compound may be used as a racemic mixture, an enantiomerically enriched mixture, or the racemic mixture may be separated using well-known techniques and an individual enantiomer may be used alone.

In the event that the present compound may exist in tautomeric forms, such as keto-enol tautomers, each tautomeric form is contemplated as being included within this invention whether existing in equilibrium or predominantly in one form.

The present invention also provides a method of treatment of diseases caused by pathological levels of either one or both YAK1 and YAK3 kinases, which method comprises administering to an animal, particularly a mammal, most particularly a human, in need thereof one or more compounds of Formula II. In addition to the above-identified compounds of Formula I, the compounds of Formula II comprise compounds wherein $R_1$ of Formula I is additionally selected from the group consisting of: halogen, $C_{1-6}$alkyl, and aryl.

Thus, the compounds of Formula II used in the present method may be conveniently defined as follows:

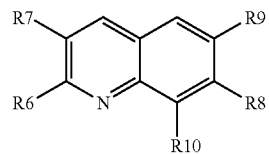

(II)

wherein:
$R_6$ is selected from the group consisting of: —NH—$C_{1-6}$ alkyl, —NH—$C_{3-7}$ cycloalkyl, —NH—$C_{3-7}$ cycloheteroalkyl, —NH-aryl, —NH-Het, —O—$C_{1-6}$ alkyl, —O—$C_{3-7}$ cycloalkyl, —O—$C_{3-7}$ cycloheteroalkyl, —O-aryl, —O-Het, —S—$C_{1-6}$ alkyl, —S—$C_{3-7}$ cycloalkyl, —S—$C_{3-7}$ cycloheteroalkyl, —S-aryl, —S-Het, $C_{1-6}$ alkyl, aryl, —$C_{3-7}$ cycloalkyl, —$C_{3-7}$ cycloheteroalkyl, and halogen;

$R_7$ is selected from the group consisting of: —$CO_2H$, —$CONH_2$, —CHNOH, —$CO_2R'$, —$CH_2OH$, —CHO, —CONHR", —CONHCOR", and —$CONHSO_2R$";

$R_8$ is selected from the group consisting of: —H, —OH, —$C_{1-6}$ alkyl, —$C_{3-7}$ cycloalkyl, aryl, Het, —O—$C_{1-6}$ alkyl, —O—$C_{3-7}$ cycloalkyl, —O-aryl, —O-Het, —S—$C_{1-6}$ alkyl, —S—$C_{3-7}$ cycloalkyl, —S-aryl, —S-Het, —NH—$C_{1-6}$ alkyl, —NH—$C_{3-7}$ cycloalkyl, —NH-aryl, —NH-Het and halogen;

$R_9$ is selected from the group consisting of: —H, —$C_{1-6}$ alkyl, —$C_{3-7}$ cycloalkyl, aryl, Het, —O—$C_{1-6}$ alkyl, —O—$C_{3-7}$ cycloalkyl, —O-aryl, —O-Het, —S—$C_{1-6}$ alkyl, —S—$C_{3-7}$ cycloalkyl, —S-aryl, —S-Het, —NH—$C_{1-6}$ alkyl, —NH—$C_{3-7}$ cycloalkyl, —NH-aryl, —NH-Het and halogen;

$R_8$ and $R_9$ can form a 5 to 7 membered ring comprising 0–3 heteroatoms independently selected from the group consisting of: O, N, and S;

$R_{10}$ is selected from the group consisting of: H and halogen;

R' is selected from the group consisting of: $C_{1-6}$ alkyl, $C_{3-7}$ cycloalkyl, and $C_{3-7}$ cycloheteroalkyl; and R" is selected from the group consisting of: $C_{1-6}$ alkyl, $C_{3-7}$ cycloalkyl, $C_{3-7}$ cycloheteroalkyl, aryl, and Het;

or a pharmaceutically acceptable salt, hydrate or solvate thereof.

Preferably used in the present methods are the following compounds of formula II wherein:
$R_6$ is preferably selected from the group consisting of: : —NH—$C_{1-6}$ alkyl, —NH-aryl, —NH-Het, —O-aryl, —O-Het, —S-aryl, —S-Het, —$C_{3-7}$ cycloheteroalkyl, and halogen;

$R_7$ is preferably selected from the group consisting of: —$CO_2H$, —$CONH_2$, and —$CO_2R'$;

$R_8$ is preferably selected from the group consisting of: —H, —$C_{1-6}$ alkyl, —O—$C_{1-6}$ alkyl, —S—$C_{1-6}$ alkyl, and halogen; and $R_9$ is preferably selected from the group consisting of: —H, —O—$C_{1-6}$ alkyl, —S—$C_{1-6}$ alkyl, and halogen.

When $R_7$ is —$CO_2R'$, R' is preferably selected from the group consisting of: —$C_{1-6}$ alkyl, and —$C_{3-7}$ cycloalkyl.

More preferably used in the present methods are compounds of formula II wherein:
$R_6$ is more preferably selected from the group consisting of: —NH—$C_{1-6}$ alkyl, —NH-aryl, —NH-Het, —$C_{3-7}$ cycloheteroalkyl and halogen;

$R_7$ is more preferably selected from the group consisting of: —$CO_2H$ and —$CONH_2$;

$R_8$ is more preferably selected from the group consisting of: —H, —$C_{1-6}$ alkyl, —O—$C_{1-6}$ alkyl, —S—$C_{1-6}$ alkyl, and halogen; and $R_9$ is more preferably selected from the group consisting of: —H and halogen, even more preferably $R_9$ is H; and $R_{10}$ is more preferably —H.

When, in $R_6$, halogen is chlorine:
$R_7$ is selected from the group consisting of: —$CO_2H$, —$CONH_2$, —CHNOH and —$CO_2R'$;

$R_8$ is selected from the group consisting of: —H, —OH, —$C_{1-6}$ alkyl, —O—$C_{1-6}$ alkyl, —O—$C_{3-7}$ cycloalkyl, —S—$C_{1-6}$ alkyl, and halogen;

$R_9$ is selected from the group consisting of: —H, —$C_{1-6}$ alkyl, —O—$C_{1-6}$ alkyl, most preferably wherein —$C_{1-6}$ alkyl is —$CH_3$, —S—$C_{1-6}$ alkyl, most preferably wherein —$C_{1-6}$ alkyl is —$CH_3$, and halogen; and $R_{10}$ is selected from the group consisting of: —H and halogen.

Even more preferred are compounds of Formula II used in the present method wherein, in $R_6$:
NH-aryl is most preferably selected from the group consisting of: methylphenylamino, especially 3-methylphenylamino (also known as m-tolylamino); ethylphenylamino, especially 3-ethylphenylamino, 4-ethylphenylamino; cyclohexylphenylamino, especially 4-cyclohexylphenylamino; dimethylphenylamino, especially 3,4-dimethylphenylamino; chlorophenylamino, especially 2-chlorophenylamino, 3-chlorophenylamino, 4-chlorophenylamino; fluorophenylamino, especially 2-fluorophenylamino, 4-fluorophenylamino; iodophenylamino, especially 4-iodophenylamino; chlorobenzylamino, especially 4-chlorobenzylamino; morpholinophenylamino, especially 4-morpholin-4-yl-phenylamino; cyanophenylamino, especially 3-cyanophenylamino, 4-cyanophenylamino; ethoxyphenylamino, especially 4-ethoxyphenylamino; dimethoxyphenylamino, especially 3,4-dimethoxyphenylamino, phenoxyphenylamino, especially 4-phenoxyphenylamino; and fluoroethoxyphenylamino, especially 2-fluoro-3-ethoxyphenylamino;

—NH-Het is most preferably selected from the group consisting of: quinolinylamino, especially quinolin-3-ylamino, quinolin-5-ylamino, quinolin-8-ylamino; pyridinylamino, especially pyridin-3-ylamino; and methoxy-pyridinylamino, especially 6-methoxy-pyridin-3-ylamino;

—$C_{3-7}$ cycloheteroalkyl is most preferably piperidino, especially N-piperidino;

—NH—$C_{1-6}$ alkyl is preferably propylamino, especially 2-propylamino; and halogen is preferably chloro; and in $R_8$:
—$C_{1-6}$ alkyl is most preferably selected from the group consisting of: methyl and ethyl;

—O—$C_{1-6}$ alkyl is most preferably methoxy;

—S—$C_{1-6}$ alkyl is most preferably methylsulfanyl; and halogen is most preferably chloro.

Especially preferred compounds of the present invention for use in the present methods are:
2-(3-Chloro-phenylamino)-7-methoxy-quinoline-3-carboxylic acid;
2-Chloro-7-methoxy-quinoline-3-carboxylic acid;
7-Chloro-2-(3-chloro-phenylamino)-quinoline-3-carboxylic acid; 2-(3-Chloro-phenylamino)-7-methylsulfanyl-quinoline-3-carboxylic acid;
2-(4-Chloro-phenylamino)-7-methoxy-quinoline-3-carboxylic acid;
2-(3-Chloro-phenylamino)-7-methoxy-quinoline-3-carboxylic acid amide
2-(4-Chloro-benzylamino)-7-methoxy-quinoline-3-carboxylic acid;
7-Methoxy-2-(4phenoxy-phenylamino)-quinoline-3-carboxylic acid
7-Methoxy-2-(4-morpholin-4-yl-phenylamino)-quinoline-3-carboxylic acid;
2-(3-Chloro-phenylamino)-quinoline-3-carboxylic acid;
2-(3-Chloro-phenylamino)-7-methyl-quinoline-3-carboxylic acid;2-Chloro-7-methyl-quinoline-3-carboxylic acid;
2-(3-Chloro-phenylamino)-6-methoxy-quinoline-3-carboxylic acid;
2-(3-Chloro-phenylamino)-7-ethyl-quinoline-3-carboxylic acid;
2-(3-Cyano-phenylamino)-7-methoxy-quinoline-3-carboxylic acid;
7-Methoxy-2-m-tolylamino-quinoline-3-carboxylic acid;
2-(4-Ethoxy-phenylamino)-7-methoxy-quinoline-3-carboxylic acid;
2-(4-Cyclohexyl-phenylamino)-7-methoxy-quinoline-3-carboxylic acid;
2-(4-Fluoro-phenylamino)-7-methoxy-quinoline-3-carboxylic acid;
2-(2-Chloro-phenylamino)-7-methoxy-quinoline-3-carboxylic acid;
2-(4-Ethyl-phenylamino)-7-methoxy-quinoline-3-carboxylic acid;
2-(3-Ethyl-phenylamino)-7-methoxy-quinoline-3-carboxylic acid;
2-(4-Cyano-phenylamino)-7-methoxy-quinoline-3-carboxylic acid;
7-Methoxy-2-(quinolin-3-ylamino)-quinoline-3-carboxylic acid;
2-(4-Iodo-phenylamino)-7-methoxy-quinoline-3-carboxylic acid;
7-Methoxy-2-(pyridin-3-ylamino)-quinoline-3-carboxylic acid;
7-Methoxy-2-(6-methoxy-pyridin-3-ylamino)-quinoline-3-carboxylic acid;
7-Methoxy-2-(quinolin-8-ylamino)-quinoline-3-carboxylic acid;
7-Methoxy-2-(quinolin-5-ylamino):quinoline-3-carboxylic acid;
2-(3,4-Dimethoxy-phenylamino)-7-methoxy-quinoline-3-carboxylic acid;
2-(3,4-Dimethyl-phenylamino)-7-methoxy-quinoline-3-carboxylic acid;
2-(2-Fluoro-phenylamino)-7-methoxy-quinoline-3-carboxylic acid;
2-(4-Ethoxy-2-fluoro-phenylamino)-7-methoxy-quinoline-3-carboxylic acid;
7-Methoxy-2-piperidin-1-yl-quinoline-3-carboxylic acid; and7-Methoxy-2-propylamino-quinoline-3-carboxylic acid.
2-Chloro-7-methoxy-quinoline-3-carboxylic acid may also be named 2-chloro-3-carboxy-7-methoxy-quinoline; and 2-chloro-7-methyl-quinoline-3-carboxylic acid; may also be named 2-chloro-3-carboxy-7-methyl-quinoline.

More especially preferred compounds of the present invention for use in the present Methods are:
2-(3-Chloro-phenylamino)-7-methoxy-quinoline-3-carboxylic acid;
7-Chloro-2-(3-chloro-phenylamino)-quinoline-3-carboxylic acid; 2-(3-Chloro-phenylamino)-7-methylsulfanyl-quinoline-3-carboxylic acid;
2-(4-Chloro-phenylamino)-7-methoxy-quinoline-3-carboxylic acid;
2-(4-Chloro-benzylamino)-7-methoxy-quinoline-3-carboxylic acid;
7-Methoxy-2-(4-phenoxy-phenylamino)-quinoline-3-carboxylic acid;
2-Chloro-7-methyl-quinoline-3-carboxylic acid;
2-(3-Cyano-phenylamino)-7-methoxy-quinoline-3-carboxylic acid;
7-Methoxy-2-m-tolylamino-quinoline-3-carboxylic acid;
2-(4-Ethoxy-phenylamino)-7-methoxy-quinoline-3-carboxylic acid
2-(4-Cyclohexyl-phenylamino)-7-methoxy-quinoline-3-carboxylic acid;
2-(4-Fluoro-phenylamino)-7-methoxy-quinoline-3-carboxylic acid;
2-(2-Chloro-phenylamino)-7-methoxy-quinoline-3-carboxylic acid;
2-(4-Ethyl-phenylamino)-7-methoxy-quinoline-3-carboxylic acid;
2-(3-Ethyl-phenylamino)-7-methoxy-quinoline-3-carboxylic acid;
2-(4-Cyano-phenylamino)-7-methoxy-quinoline-3-carboxylic acid;
7-Methoxy-2-(quinolin-3-ylamino)-quinoline-3-carboxylic acid;
2-(4-Iodo-phenylamino)-7-methoxy-quinoline-3-carboxylic acid;
7-Methoxy-2-(6-methoxy-pyridin-3-ylamino)-quinoline-3-carboxylic acid;
7-Methoxy-2-(quinolin-8-ylamino)-quinoline-3-carboxylic acid;
7-Methoxy-2-(quinolin-5-ylamino)-quinoline-3-carboxylic acid;
2-(3,4-Dimethoxy-phenylamino)-7-methoxy-quinoline-3-carboxylic acid;
2-(2-Fluoro-phenylamino)-7-methoxy-quinoline-3-carboxylic acid; and
2-(4-Ethoxy-2-fluoro-phenylamino)-7-methoxy-quinoline-3-carboxylic acid.

Most especially preferred compounds of the present invention for use in the present methods are:
2-(3-Chloro-phenylamino)-7-methoxy-quinoline-3-carboxylic acid;
2-(3-Chloro-phenylamino)-7-methylsulfanyl-quinoline-3-carboxylic acid;
2-(4-Chloro-phenylamino)-7-methoxy-quinoline-3-carboxylic acid;
2-Chloro-7-methyl-quinoline-3-carboxylic acid;
2-(3-Cyano-phenylamino)-7-methoxy-quinoline-3-carboxylic acid;
7-Methoxy-2-m-tolylamino-quinoline-3-carboxylic acid;
2-(4-Ethoxy-phenylamino)-7-methoxy-quinoline-3-carboxylic acid;
2-(4-Fluoro-phenylamino)-7-methoxy-quinoline-3-carboxylic acid;

2-(2-Chloro-phenylamino)-7-methoxy-quinoline-3-carboxylic acid;
2-(4-Ethyl-phenylamino)-7-methoxy-quinoline-3-carboxylic acid;
2-(3-Ethyl-phenylamino)-7-methoxy-quinoline-3-carboxylic acid;
2-(4-Cyano-phenylamino)-7-methoxy-quinoline-3-carboxylic acid;
2-(4-Iodo-phenylamino)-7-methoxy-quinoline-3-carboxylic acid;
7-Methoxy-2-(quinolin-8-ylamino)-quinoline-3-carboxylic acid;
7-Methoxy-2-(quinolin-5-ylamino)-quinoline-3-carboxylic acid;
2-(2-Fluoro-phenylamino)-7-methoxy-quinoline-3-carboxylic acid; and
2-(4-Ethoxy-2-fluoro-phenylamino)-7-methoxy-quinoline-3-carboxylic acid.

DEFINITIONS

"hYAK1 kinase" means human YAK 1 kinase.
"hYAK3 kinase" means human YAK3 kinase.
"$C_{1-6}$alkyl" as applied herein is meant to include substituted and unsubstituted methyl, ethyl, n-propyl, isopropyl, n-butyl, isobutyl and t-butyl, pentyl, n-pentyl, isopentyl, neopentyl and hexyl and the simple aliphatic isomers thereof. Any $C_{1-6}$alkyl group may be optionally substituted independently by one to five halogens, SR''', OR''', or N(R''')$_2$, where R''' is $C_{1-6}$alkyl.
"$C_{3-7}$ cycloalkyl" as applied herein is meant to include substituted and unsubstituted cyclopropane, cyclobutane, cyclopentane, cyclohexane and cycloheptane.
"$C_{3-7}$ cycloheteroalkyl" as applied herein is meant to include 3-, 4-, 5-, 6-, and 7-membered rings having at least one, but no more than three, ring heteroatom(s) selected from the group consisting of: N, O, and S. Examples include, but are not limited to, piperidine, piperazine, morpholine, thiomorpholine, tetrahydrofuran, tetrahydrothiophene, pyrrolidine, azepane, oxepane, and thiepane.
"Halogen" means F, Cl, Br, and I.
"Ar" or "aryl" means phenyl, benzyl or naphthyl, optionally substituted by one or more of Ph, Het, Ph-$C_{0-6}$alkyl; Het-$C_{0-6}$alkyl; $C_{1-6}$alkoxy; Ph-$C_{0-6}$alkoxy; Het-$C_{0-6}$alkoxy; OH, $(CH_2)_{1-6}NR^{11}R^{12}$; $O(CH_2)_{1-6}NR^{11}R^{12}$; $C_{1-6}$alkyl, $C_{3-7}$cycloalkyl, OR'''', N(R'''')$_2$, SR'''', CF$_3$, NO$_2$, CN, CO$_2$R'''', CON(R''''), F, Cl, Br or I; where R$^{11}$ and R$^{12}$ are H, $C_{1-6}$alkyl, Ph-$C_{0-6}$alkyl, naphthyl-$C_{0-6}$alkyl or Het-$C_{0-6}$alkyl; and R'''' is H, phenyl, naphthyl, Het or $C_{1-6}$alkyl.
The term "—N—$C_{1-6}$alkyl" includes both mono- and di-$C_{1-6}$alkyl substitutions on the N, including di-substitutions resulting in an N-containing cyclic ring, e.g.,

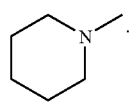

As used herein "Het" or "heterocyclic" represents a stable 5- to 7-membered monocyclic, a stable 7- to 10-membered bicyclic, or a stable 11- to 18-membered tricyclic heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure, and may optionally be substituted with one or two moieties selected from $C_{0-6}$Ar, $C_{1-6}$alkyl, OR$^{13}$, N(R$^{13}$)$_2$, SR$^{13}$, CF$_3$, NO$_2$, CN, CO$_2$R$^{13}$, CON(R$^{13}$), F, Cl, Br and I, where R$^{13}$ is —H, phenyl, naphthyl, or $C_{1-6}$alkyl. Examples of such heterocycles include, but are not limited to, piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, pyridinyl, pyrazinyl, oxazolidinyl, oxazolinyl, oxazolyl, isoxazolyl, morpholinyl, thiazolidinyl, thiazolinyl, thiazolyl, quinuclidinyl, indolyl, quinolinyl, isoquinolinyl, benzimidazolyl, benzopyranyl, benzoxazolyl, furyl, pyranyl, tetrahydrofuryl, tetrahydropyranyl, thienyl, benzoxazolyl, thiamorpholinyl sulfoxide, thiamorpholinyl sulfone, and oxadiazoly, as well as triazolyl, thiadiazolyl, oxadiazolyl, isoxazolyl, isothiazolyl, imidazolyl, pyridazinyl, pyrimidinyl, triazinyl and tetrazinyl which are available by routine chemical synthesis and are stable. The term heteroatom as applied herein refers to oxygen, nitrogen and sulfur.

The term "R$_3$ and R$_4$ (as well as "R$_8$ and R$_9$") can form a 5 to 7 membered ring comprising 0–3 heteroatoms independently selected from the group consisting of: O, N, and S" includes, but is not limited to: methylenedioxy, imadazoyly, pyrrolyl, dihydropyrrolyl, thiophenyl, dihydrothiophenyl, furanyl, dihydrofuranyl or triazinyl.

Certain radical groups are abbreviated herein. Thus, t-Bu refers to the tertiary butyl radical, Ph refers to the phenyl radical.

Certain reagents are abbreviated herein. DMF refers to dimethyl formamide, and DMSO refers to dimethyl sulfoxide.

METHOD OF PREPARATION

Methods for preparing compounds of the Formula I are shown in Schemes 1–3

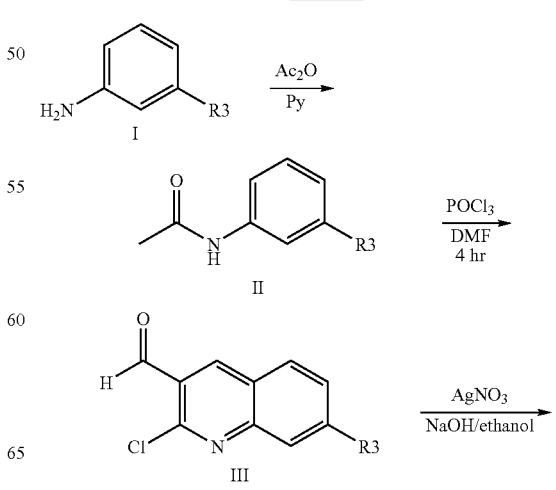

-continued

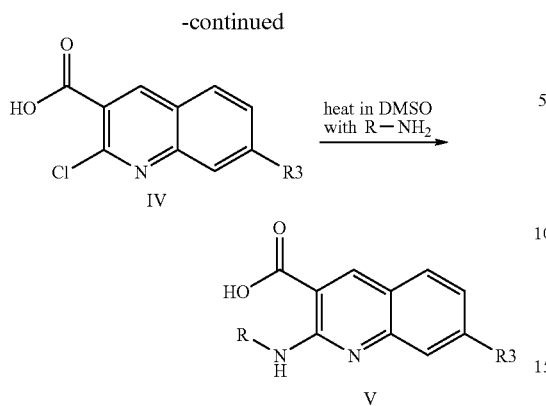

IV

V

In general, the synthetic methods used herein are those detailed in *J. C. S. Perkin* 1, 1981, 5, 1520–30 and *J. Het. Chem.* 1991, 28(5), 1339–40 for preparing substituted carboxy quinolines. Briefly, a substituted aniline (I) is acylated with acetic anhydride in pyridine to give the resulting acetanilide (II). Treatment of the acetanilide (II) with POCl₃ in DMF gives a 2-chloride-3-formyl quinoline (III). Oxidation with AgNO₃ in basic ethanol gives the corresponding 2-chloride-3-carboxy quinoline (IV). The 2-chloro can be replaced with either aryl or alkyl amines in DMSO to give the resulting 2-substituted quinoline (V) (Scheme 1).

Scheme 2

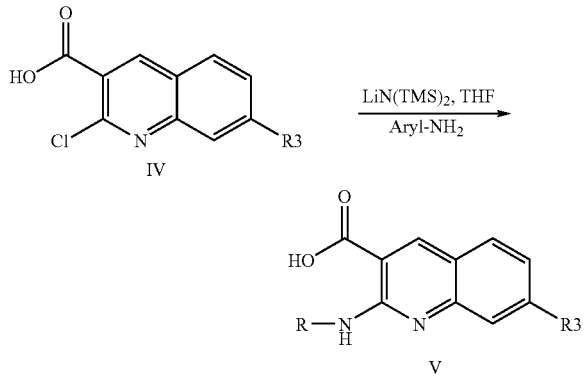

IV

V

Alternatively, the novel method of Scheme 2 may be used, in which the 2-chloride-3-carboxy quinoline (IV) is treated with an aryl amine in the presence of excess of lithium hexamethyldisilazane in THF (−70 C to RT) to give the 2-substituted quinoline (V) (Scheme 2). For alkyl amines, excess of the lithium salt of the particular alkyl amine is used in place of lithium hexamethyldisilazane. The novel method is further disclosed in Example 13.

Scheme 3

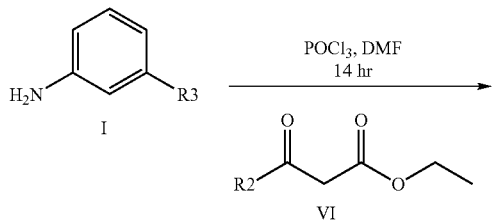

-continued

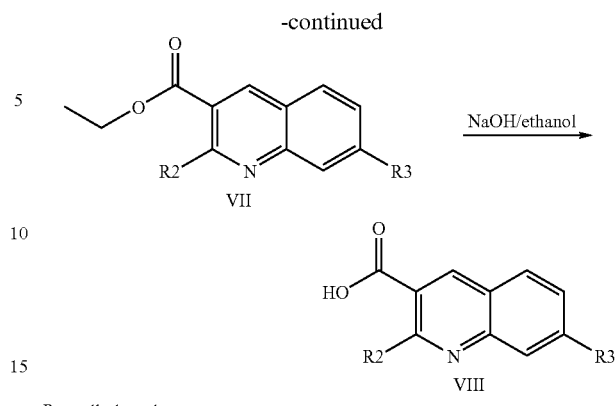

VII

VIII $R_2$ = alkyl, aryl

In the cases where $R_2$ is alkyl or aryl, the aniline I can be treated with POCl₃ and the keto ester VI to give VII which is subsequently converted by hydrolysis to VII.

The starting materials used herein are commercially available or are prepared by routine methods well known to those of ordinary skill in the art and can be found in standard reference books, such as the Compendium of Organic Synthetic Methods, Vol. I–VI (published by Wiley-Interscience).

Acid addition salts of the compound of Formula I are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic acid.

UTILITY OF THE PRESENT INVENTION

This invention also provides a pharmaceutical composition which comprises at least one compound according to Formula I and a pharmaceutically acceptable carrier, excipient or diluent. These pharmaceutical compositions are useful in the methods of treatment of this invention. Pharmaceutical compositions comprising at least one compound of Formula II and a pharmaceutically acceptable carrier, excipient or diluent are also useful in the methods of treatment of this invention. Accordingly, at least one compound of Formula I or Formula II may be used in the manufacture of a medicament. Pharmaceutical compositions of a compound of Formula I or Formula II prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water, or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride, or sodium citrate.

Alternately, this compound may be encapsulated, tableted, or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule.

For rectal administration, the compound of this invention may also be combined with excipients such as cocoa butter, glycerin, gelatin or polyethylene glycols and molded into a suppository.

Compounds of Formula I and Formula II are useful as inhibitors of either one or both hYAK1 and hYAK3 kinases. The present invention also provides useful compositions and formulations of said compounds, including pharmaceutical compositions and formulations of said compounds.

The present compounds are useful for treating disease states in which either one or both hYAK1 and hYAK3 kinases are implicated, especially diseases of the hematopoietic system, including anemias due to renal insufficiency or to chronic disease, such as autoimmunity or cancer and drug-induced anemias, polycythemia, myelodysplastic syndrome, aplastic anemia and myelosuppression; cytopenia; and are also useful for controllinging male fertility, especially for the purpose of achieving contraception.

The present invention also provides methods of treatment of diseases caused by pathological levels of either one or both YAK1 and YAK3 kinases, especially diseases of the hematopoietic system, including anemias due to renal insufficiency or to chronic disease, such as autoimmunity or cancer and drug-induced anemias, polycythemia, myelodysplastic syndrome, aplastic anemia and myelosuppression; cytopenia; and also a method of controllinging male fertility, especially for the purpose of achieving contraception, which methods comprise administering to an animal, particularly a mammal, most particularly a human, in need thereof one or more compounds of Formula II.

The present method is especially useful in treating diseases of the hematopoietic system, particularly anemias. Such anemias include an anemia selected from the group comprising: aplastic anemia and myelodysplastic syndrome. Such anemias also include those wherein the anemia is a consequence of a primary disease selected from the group consisting of: cancer, leukemia and lymphoma. Such anemias also include those wherein the anemia is a consequence of a primary disease selected from the group consisting of: renal disease, failure or damage. Such anemias include those wherein the anemia is a consequence of chemotherapy or radiation therapy, in particular wherein the chemotherapy is chemotherapy for cancer or AZT treatment for HIV infection. Such anemias include those wherein the anemia is a consequence of a bone marrow transplant or a stem cell transplant. Such anemias also include anemia of newborn infants. Such anemias also include those which are a consequence of viral, fungal, microbial or parasitic infection.

The present invention provides a method of enhancement of normal red blood cell numbers. Such enhancement is desireable for a variety of purposes, especially medical purposes such as preparation of a patient for transfusion and preparation of a patient for surgery.

The present invention also provides a method of lowering normal levels of either one or both hYAK1 and hYAK3 to achieve a desired clinical effect, especially controlling male fertility to achieve contraception.

In accordance with this invention, an effective amount of a compound of Formula II is administered to inhibit the hYAK1 and/or hYAK3 kinase implicated in a particular condition or disease. Of course, this dosage amount will further be modified according to the type of administration of the compound. For example, for acute therapy, parenteral administration of the compound of Formula II is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg preferably between 0.1 and 10 mg/kg, in a manner to maintain the concentration of drug in the plasma at a concentration effective to inhibit hYAK1 and/or hYAK3. The compound is administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

Prodrugs of the compounds of the present invention may be prepared by any suitable method. Where the prodrug moiety is a ketone functionality, specifically ketals and/or hemiacetals, the conversion may be effected in accordance with conventional methods.

The compounds of this invention may also be administered orally to the patient, in a manner such that the concentration of drug is sufficient to inhibit bone resorption or to achieve any other therapeutic indication as disclosed herein. Typically, a pharmaceutical composition containing the compound is administered at an oral dose of between about 0.1 to about 100 mg/kg in a manner consistent with the condition of the patient. Preferably the oral dose would be about 0.5 to about 20 mg/kg. No unacceptable toxicological effects are expected when compounds of the present invention are administered in accordance with the present invention.

BIOLOGICAL ASSAYS

The compounds of this invention may be tested in one of several biological assays to determine the concentration of compound which is required to have a given pharmacological effect.

Kinase Assays Using Ser164 as the Phosphoacceptor

The source of Ser164 peptide The Ser164 (LGGRD-SRSGSPMARR-OH) peptide was purchased from California Peptide Research Inc. (Napa, Calif.), and its purity was determined by HPLC. The peptide contained 15 amino acids, and its calculated molecular mass was 1601.82 dalton. Solid sample was dissolved at 5 mM in ice-cold kinase assay buffer (see later), aliquoted, and stored at −20° C. until use.

The source of enzyme:

1) hYAK1: DET1/DET2-tagged full length hYAK1 was expressed in Drosophila sf9 cells and purified to >95% purity using Ni column chromatography. The purified protein migrated on SDS gels as a single band an apparent molecular mass of 62 kDa. Samples were stored at −80° C. until use.

2) hYAK3: Glutathione-S-Transferase (GSI)/Factor Xa-tagged hYAK3B was expressed in baculovirus cells and purified to about 50% purity using Glutathione Sepharose 4B column chromatography, followed by Ni-NTA column chromatography. Samples were stored at −80° C. until use.

3) Yeast YAK1: Full length and an amino-terminally truncated (amino acids 148–807, termed ΔN) hemagglutinin (HA)-tagged yeast YAK1 was each expressed in a strain of *S. cerevisiae* lacking the endogenous YAK1 gene and all three PKA genes. Cultures for experiments were grown in liquid Sc-His to an $OD_{600}$ of at least 1.0, washed with Sc-His g/r, resuspended in Sc-His g/r to twice the original volume and grown for 16–24 h at RT. Cells were washed once with $H_2O$ and the pellets stored at −80° C. until use. To prepare lysates, cell pellets were thawed and resuspended at 1 ml/100 ml of original culture in lysis buffer (LB) containing 50 mM Tris pH 7.5, 150 mM NaCl, 10 µg/ml each aprotinin, leupeptin and TLCK, 0.1 mM PMSF, 50 mM NaF, 1 mM Na vanadate, 10 mM β-glycerophosphate. Following the addition of 0.5 ml sterile acid-washed glass beads, cells were disrupted via ten, 30 sec intervals of vortexing. NP40 was added to a 2% final concentration followed by rocking at 4° C. for 30–50 min. Lysates were clarified by high speed centrifugation, and the supernatants were stored at −80° C. until use. Each form of yeast YAK1 was immunoprecipitated from the detergent extracts using anti-HA mAb.

Immune Complex Protein Kinase Assay for Yeast YAK1: Yeast cellular extracts were immunoprecipitated by rocking overnight at 4° C. with 4 µg of the anti-HA tag antibody and 100 µl of 20% suspension of protein A agarose (GIBCO-BRL) in LB that contained 1% NP-40. Samples were then washed twice with LB and once with basic kinase assay buffer (25 mM Hepes, pH 7.5; 1 mM DTT; 10 mM β-glycerol phosphate; 0.2 mM NaV). Washed immune complexes were suspended in 20 µl of basic kinase assay buffer that contained 0.1 mM ATP, 3 µCi of [γ-$^{32}$P]ATP, 10 MM $MgCl_2$, plus either bovine MBP or the Ser164 peptide. After incubation for 15 min at 30° C., the reactions were stopped by adding 20 µl of 0.15 M phosphoric acid. Phosphorylated substrates were isolated by spotting 20 µl of each sample on phosphocellulose (p81) filters. Filters were washed 3 times with 75 mM phosphoric acid followed by 3 times with $H_2O$, and counted for $^{32}P$ incorporation using β-scintillation counter.

Kinase assay of purified hYAK1 and hYAK3: Assay was performed in 96 well Minisorp plates (Costar, Catalog No. 3356). Reactions (in 30 ul volume) mix contained in final concentrations 25 mM Hepes buffer, pH 7.5; 0.2 mM sodium vanadate; 10 MM $MgCl_2$; 1 mM DTT; 10 mM β-glycerol phosphate; 0.1% BSA; 0.1 mM ATP, 2.5 µCi of [γ-$^{32}$P]ATP; purified hYAK1 (1–5 ng/assay), or purified hYAK3 (50–100 ng/assay); and either bovine MBP or the Ser164 peptide used at the concentrations indicated below and the legends to figures. Reactions were incubated for 20 min at 37° C., and were stopped by adding 10 µl of 0.3 M phosphoric acid. Phosphorylated substrates were isolated by spotting 20 µl of p81 filters, and processed as detailed earlier.

Figure 2:
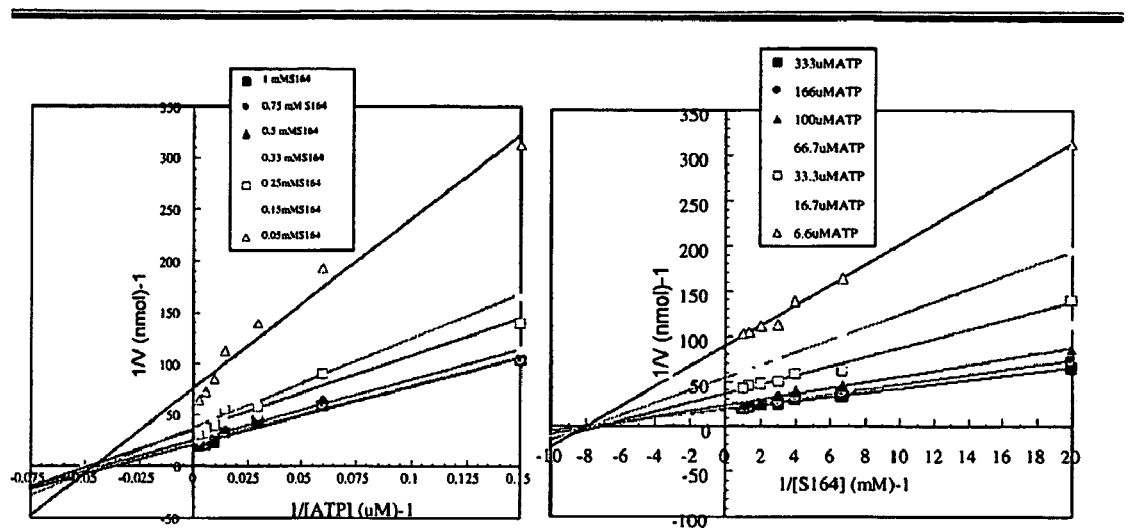
FIG. 2 shows double reciprocal plots (1/V vs. 1/[substrate]) with S164 peptide as the phosphate acceptor.

This same assay can be performed on a FlashPlate format in which the plate is coated with MBP or with the S164 peptide by incubation overnight at 4° C. in 100 ul of either substrate dissolved in Sodium Carbonate buffer, pH 8.8. When coating with MBP, a solution of 100 ug/ml MBP was used to coat wells with 100 ul (10 ug) MBP per well. When coating with Ser164, a solution of 0.4 mg/ml (0.25 mM) was used to coat wells with 100 ul (40 ug) Ser164 per well. An example of a FlashPlate assay protocol and typical results are given below:

FlashPlate Protocol
1. Coat Maxisorp plates (Nunk, Immunoplate, Maxisorp™) with MBP or Ser164 as above.
2. Wash plates once with kinase assay buffer (KB): 25 mM Hepes, pH 7.5; 0.2 mM NaV; 10 mM.-glycerol phosphate; 1 mM Na pyrophosphate
3. Add enzyme (Ni-hYAK1, diluted in KB), DMSO or inhibitors (in KB) and keep on ice 30 min
4. Add KB containing Mg/AJP to a [final] of 0.1 mM [.-33P]ATP and 10 mM $MgCl_2$
5. Incubate with shaking, 1–2 hrs, RT
6. Aspirate and wash 6×0.5 ml KB
7. Read 33P incorporation in FP reader
8. Blank=No enzyme added
9. Reaction volume: 25, 50 or 100 ul
10. 0.5 or 1.0 uCi 33P/0.1 mM ATP
11. MBP-FP better than basic FP (in house coating)
12. 37° C. incubation was not better (several time points)
13. Other incubation times at RT were not better Results:

Each kinase phosphorylated the Ser164 peptide with much higher specific activity than MBP (FIG. 1). Steady state kinetic constants of hYak1 reaction were generated by varying both substrates simultaneously and fitting enzyme velocity as a function of each substrate concentration. Double reciprocal plots (1/V vs. 1/[Substrate]) with S164 peptide as the phosphate acceptor are shown in FIG. 2. GraphFit analysis of the results generated the following steady state kinetic constants:

$K_m[ATP]=42\pm7$ uM.

$K_m[S164]=160\pm14$ uM.

$V_{max}=51\pm6$ umol/mg.

$k_{cat}=160\pm19$ min$^{-1}$.

Typical results of FlashPlate are shown below

FlashPlate Typical Results

| | |
|---|---|
| Signal to noise ratio: | >7 fold |
| Blanks: | 30–80 cpm |
| [Ni-hYAK1]: | As low as 20 ng/reaction (5 nM) for 100 ul reactions |
| | As low as 8 ng/reaction (5 nM) for 25 ul reactions |
| 33P: | As low as 0.5 uCi |
| Kinase inhibitors: | Potency comparable to tube assay: |
| | SKF-108752 IC50:    0.1 ug hYAK1: 0.19 uM |
| | 0.3 ug hYAK1: 0.13 uM; 0.16 uM |
| | K252a IC50    (0.3 ug hYAK1): 0.552 uM; 0.427 uM |
| Specific Activity: | At 20 ng enzyme, MBP gave 58 ± 3 (n = 6), and Ser164 gave 484 ± 63 nmol/mg protein (n = 6), |
| DMSO: | No effect up to 3% |
| Variability: | <10% (between wells and from plate to plate). |

The $IC_{50}$ of the present compounds, as measured in the assays described above, respecting hYAK1 is about 0.01 to about 10 uM, and about 0.03 to about 10 uM respecting hYAK3.

The skilled artisan would consider any compound exhibiting an $IC_{50}$ value of less than 1 uM to be a potential lead compound for further research, and an inhibitor exhibiting an $IC_{50}$ of less than 0.05 uM to be a drug development drug candidate assuming an acceptable pathology/toxicology profile and in vivo activity.

Human Colony Forming Unit-Erythroid (CFU-E) Assay

Light density cells from human bone marrow centrifuged over Histopaque 1077 were washed and resuspended at $2.5 \times 10^6$ cells/ml in X-vivo medium. A final concentration of: cells (2.5×105/ml), fetal calf serum (25%), bovine serum albumin (1%) and methylcellulose (0.8%) in X-Vivo medium were added in a volume of 0.4 ml per well of a 24-well TC dish (Nunc). The compound of the present invention was diluted in X-vivo medium and added at final concentrations of 1 and 10 uM to the wells. All wells contained 2 U/ml erythropoietin (EPO). The cultures were incubated at 37°, 5% $CO_2$, 5% $O_2$ for seven days. Colonies were identified by microscopic examination as a group of greater than eight red, hemoglobinized cells.

Figure 3:
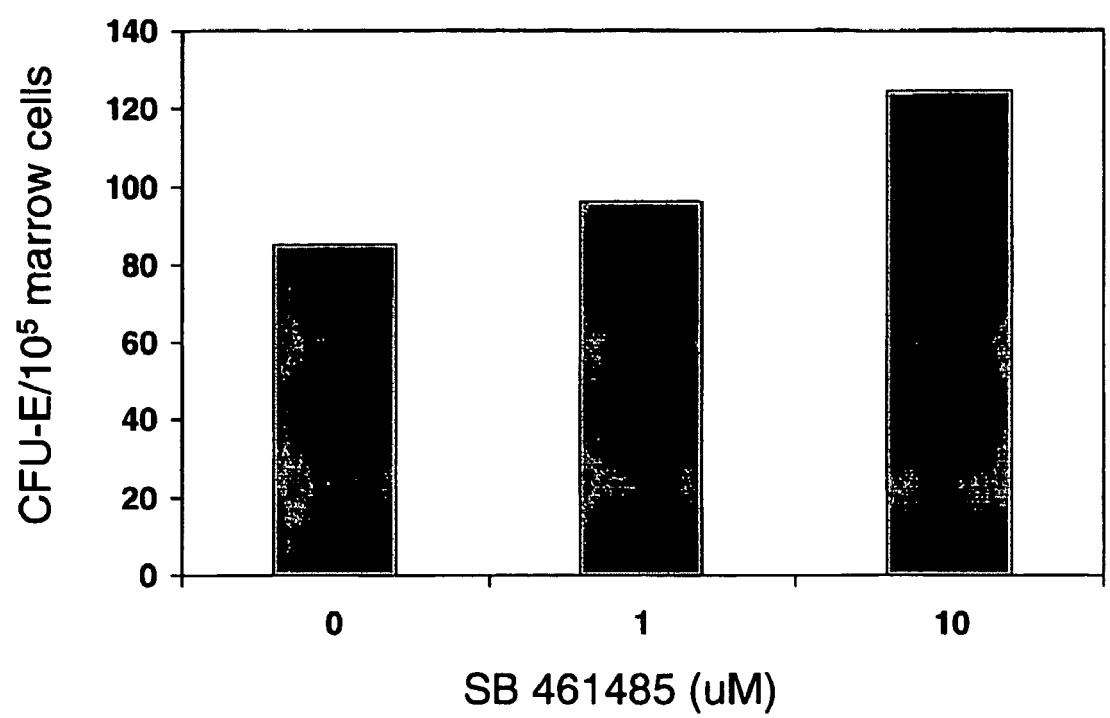
FIG. 3 shows 2-Chloro-7-methyl-quinoline-3-carboxylic acid enhances CFU-E formation in the presence of erythropoietin. The number of CFU-E colonies recovered from human bone marrow cultures grown in the presence of 2 U/ml erythropoietin and 0, 1 or 10 uM 2-chloro-7-methyl-quinoline-3-carboxylic acid was measured.

Results:

The addition of 2-chloro-7-methyl-quinoline-3-carboxylic acid to human bone marrow cultures enhanced the recovery of erthyroid colonies in the CFU-E assay (FIG. 3). In the presence of 2 U/ml erythropoietin, 10 uM of 2-chloro-7-methyl-quinoline-3-carboxylic acid enhances CFU-E recovery by 50%.

Compounds of the present invention which enhance CFU-E recovery in this assay may be useful for treatment of diseases of the hematopoietic system, as disclosed herein above.

EXAMPLES

In the following synthetic examples, unless otherwise indicated, all of the starting materials were obtained from commercial sources. Without further elaboration, it is believed that one skilled in the art can, using the preceding description, utilize the present invention to its fullest extent. These Examples are given to illustrate the invention, not to limit its scope. Reference is made to the claims for what is reserved to the inventors hereunder.

Example 1

Preparation of 2-(3-Chloro-phenylamino)-7-methoxy-quinoline-3-carboxylic acid (a) 2-Chloro-3-formyl-7-methoxy-quinoline The title compound was prepared using the method outlined in the journal *J.C.S. Perkin* 1, 1981, No. 5, 1520–30. $^1$HNMR (300 MHz, $CDCl_3$) δ 10.51 (s, 1H), 8.65 (s,1H), 7.85 (d,J=9 Hz, 1H), 7.37 (s, 1H), 7.27 (d, J=12,1H), 3.99 (s, 3H).

(b) 2-Chloro-7-methoxy-quinoline-3-carboxylic acid

The title compound was prepared using the material from example 1a following the method outlined in *J. Het. Chem.* 1991, 28(5), 1339–40 ESMS m/e $[M+H]^+$=238.5.

(c) 2-(3-Chloro-phenylamino)-7-methoxy-quinoline-3-carboxylic acid

The material from example 1b (600 mg, 2.54 mmol) and 3-chloroaniline (275 uL, 2.54 mmol) was heated at 140° C. in 20 mL xylene for 14 h. The reaction was cooled, evaporated and purified by flash chromatography (silica gel, 20% MeOH in $CHCl_3$) to give the above titled compound. ESMS m/e $[M+H]^+$=329.5.

Example 2

Preparation of 7-Chloro-2-(3-chloro-phenylamino)-quinoline-3-carboxylic acid

Following the procedure outlined in Example 1(a)–(c) using 3'-chloroacetanilide in step 1(a) and DMSO as the solvent in step (c), the title compound was prepared. ESMS m/e $[M+H]^+$=333.5.

Example 3

Preparation of 2-(3-Chloro-phenylamino)-7-methylsulfanyl-quinoline-3-carboxylic acid Following the procedure of Example 1(a)–(c) using 3'-methylthio acetanilide in step 1(a) and DMSO as the solvent in step (c) the title compound was prepared. ESMS n/e $[M+H]^+$=344.87

Example 4

Preparation of 2-(4-Chloro-phenylamino)-7-methoxy-quinoline-3-carboxylic acid

Following the procedure of Example 1(a)–(c) except using DMSO as the solvent and 4-chloroaniline in step (c), the title compound was prepared. ESMS m/e $[M+H]^+$=329.6.

Example 5

Preparation of 2-(3-Chloro-phenylamino)-7-methoxy-quinoline-3-carboxylic acid amide The material from Example (1) (128 mg, 0.35 mmol) was attached to Rink amide resin using HBtU. The reaction shook for 48 h and was washed with $CH_2Cl_2$, MeOH, and DMF. The resin was treated with 95% aq. TFA for 14 h the resin was filtered off and the liquid was evaporated to give the title compound. ESMS m/e $[M+H]^+$=328.6.

Example 6

Preparation of 2-(4-Chloro-benzylamino)-7-methoxy-quinoline-3-carboxylic acid

Following the procedure of Example 1(a)–(c) except using DMSO as the solvent and 4-chlorobenzylamine in step (c), the title compound was prepared. ESMS m/e $[M+H]^+$=343.7.

Example 7

Preparation of 7-Methoxy-2-(4-phenoxy-phenylamino)-quinoline-3-carboxylic acid

Following the procedure of Example 1(a)–(c), except using DMSO as the solvent and 4-phenoxyaniline in step (c), the title compound was prepared. ESMS m/e $[M+H]^+$=387.6.

Example 8

Preparation of 7-Methoxy-2-(4-morpholin-4-yl-phenylamino)-quinoline-3-carboxylic acid Following the procedure of Example 1(a)–(c), except using DMSO as the solvent and 4-morpholinoaniline in step (c), the title compound was prepared. ESMS m/e [M+H]$^+$=380.6.

Example 9

Preparation of 2-(3-Chloro-phenylamino)-quinoline-3-carboxylic acid

Following the procedure of Example 1(a)–(c), using acetanilide in step 1(a) and DMSO as the solvent in step (c), the title compound was prepared. ESMS m/e [M+H]$^+$=299.6.

Example 10

Preparation of 2-(3-Chloro-phenylamino)-7-methyl-quinoline-3-carboxylic acid (a) 2-Chloro-3-formyl-7-methyl-quinoline The title compound was prepared using 3'-methyl acetanilide and the method outlined in J.C.S. Perkin 1, 1981, No. 5, 1520–30 $^1$HNMR (300 MHz, CDCl$_3$) δ 10.34 (s, 1H), 8.81 (s,1H), 8.14 (d,J=9 Hz, 1H), 7.80 (s, 1H), 7.58 (d, J=9,1H), 2.57 (s, 3H).

(b) 2-Chloro-7-methyl-quinoline-3-carboxylic acid

The title compound was prepared using the material from Example 10a following the method outlined in J. Het. Chem. 1991, 28(5), 1339–40 LC ESMS m/e [M+H]$^+$=222.5 c) 2-(3-Chloro-phenylamino)-7-methyl-quinoline-3-carboxylic acid

The material from Example 10b (370 mg 1.67 mol) and 3-chloroanaline (268 ul 2.51 mmol) were heated at 140° C. in 5 mL DMSO for 14 hr. The reaction was cooled, purified by prep. hplc, (YMC CombiPrep ODS-A, 5 min. gradient 20–95% CH$_3$CN/H$_2$O with 0.1% TFA) ESMS m/e [M+H]$^+$=312.95.

Example 11

Preparation of 2-(3-Chloro-phenylamino)-6-methoxy-quinoline-3-carboxylic acid Following the procedure of Example 1(a)–(c), using p-acetanisidide in step 1(a) and DMSO as the solvent in step (c), the title compound was prepared. ESMS m/e [M+H]$^+$=329.6.

Example 12

Preparation of 2-(3-Chloro-phenylamino)-7-ethyl-quinoline-3-carboxylic acid

Following the procedure of Example 1(a)–(c), using p-acetanisidide in step 1(a) and DMSO as the solvent in step (c), the title compound was prepared. LCMS m/e [M+H]$^+$=327.2.

Example 13

Preparation of 2-(3-Cyano-phenylamino)-7-methoxy-quinoline-3-carboxylic acid The material from example 1b (250 mg, 1.05 mmol) and 3-aminobenzonitrile (140 mg, 1.1 mmol) in THF (5.5 mL) was treated at −78° C. with 5.5 mL of 1.0 M LiN(TMS)$_2$ in hexane and the resulting solution allowed to warm slowly to room temperature. After 24 h the solvent was evaporated and the residue purified by preparative hplc to give the above named compound. LCMS m/e [M+H]$^+$=320.

Example 14

Preparation of 7-Methoxy-2-m-tolylamino-quinoline-3-carboxylic acid

Following the procedure of Example 13, with m-toluidine in place of 3-aminobenzonitrile gave the above named compound. LCMS m/e [M+H]$^+$=309.

Example 15

Preparation of 2-(4-Ethoxy-phenylamino)-7-methoxy-quinoline-3-carboxylic acid Following the procedure of Example 13, with 4-ethoxyaniline in place of 3-aminobenzonitrile gave the above named compound. LCMS m/e [M+H]$^+$=339.

Example 16

Preparation of 2-(4-Cyclohexyl-phenylamino)-7-methoxy-quinoline-3-carboxylic acid Following the procedure of Example 13, with 4-cyclohexylaniline in place of 3-aminobenzonitrile gave the above named compound. LCMS m/e [M+H]$^+$=377.

Example 17

Preparation of 2-(4-Fluoro-phenylamino)-7-methoxy-quinoline-3-carboxylic acid Following the procedure of Example 13, with 4-fluoroaniline in place of 3-aminobenzonitrile gave the above named compound. LCMS m/e [M+H]$^+$=313.

Example 18

Preparation of 2-(2-Chloro-phenylamino)-7-methoxy-quinoline-3-carboxylic acid Following the procedure of Example 13, with 2-chloroaniline in place of 3-aminobenzonitrile gave the above named compound. LCMS m/e [M+H]$^+$=329.

Example 19

Preparation of 2-(4-Ethyl-phenylamino)-7-methoxy-quinoline-3-carboxylic acid Following the procedure of Example 13, with 4-ethylaniline-in place of 3-aminobenzonitrile gave the above named compound. LCMS m/e [M+H]$^+$=323.

Example 20

Preparation of 2-(3-Ethyl-phenylamino)-7-methoxy-quinoline-3-carboxylic acid

Following the procedure of Example 13, with 3-ethylaniline-in place of 3-aminobenzonitrile gave the above named compound. LCMS m/e [M+H]$^+$=323.

Example 21

Preparation of 2-(4-Cyano-phenylamino)-7-methoxy-quinoline-3-carboxylic acid

Following the procedure of Example 13, with 4-aminobenzonitrile-in place of 3-aminobenzonitrile gave the above named compound. LCMS n/e [M+H]$^+$=320.

Example 22

Preparation of 7-Methoxy-2-(quinolin-3-ylamino)-quinoline-3-carboxylic acid

Following the procedure of Example 13, with 3-aminoquinoline-in place of 3-aminobenzonitrile gave the above named compound. LCMS m/e [M+H]$^+$=346.

Example 23

Preparation of 2-(4-Iodo-phenylamino)-7-methoxy-quinoline-3-carboxylic acid

Following the procedure of Example 13, with 4iodoaniline-in place of 3-aminobenzonitrile gave the above named compound. LCMS m/e [M+H]$^+$=421.

Example 24

Preparation of 7-Methoxy-2-(pyridin-3-ylamino)-quinoline-3-carboxylic acid

Following the procedure of Example 13, with 3-aminopyridine-in place of 3-aminobenzonitrile gave the above named compound. LCMS m/e [M+H]$^+$=296.

Example 25

Preparation of 7-Methoxy-2-(6-methoxy-pyridin-3-ylamino)-quinoline-3-carboxylic acid Following the procedure of Example 13, with 5-amino-2-methoxypyridine-in place of 3-aminobenzonitrile gave the above named compound. LCMS m/e [M+H]$^+$=326.

Example 26

Preparation of 7-Methoxy-2-(3-acetamino-aminophenyl)-quinoline-3-carboxylic acid Following the procedure of Example 13, with 3-acetaminoaniline-in place of 3-aminobenzonitrile gave the above named compound. LCMS m/e [M+H]$^+$=352.

Example 27

Preparation of 7-Methoxy-2-(quinolin-8-ylamino)-quinoline-3-carboxylic acid

Following the procedure of Example 13, with 8-aminoquinoline-in place of 3-aminobenzonitrile gave the above named compound. LCMS m/e [M+H]$^+$=346.

Example 28

Preparation of 7-Methoxy-2-(quinolin-5-ylamino)-quinoline-3-carboxylic acid

Following the procedure of Example 13, with 5-aminoquinoline-in place of 3-aminobenzonitrile gave the above named compound. LCMS m/e [M+H]$^+$=346.

Example 29

Preparation of 2-(3,4-Dimethoxy-phenylamino)-7-methoxy-quinoline-3-carboxylic acid Following the procedure of Example 13, with 3,4-dimethoxyaniline-in place of 3-aminobenzonitrile gave the above named compound. LCMS m/e [M+H]$^+$=355.

Example 30

Preparation of 2-(3,4-Dimethyl-phenylamino)-7-methoxy-quinoline-3-carboxylic acid Following the procedure of Example 13, with 3,4-dimethylaniline-in place of 3-aminobenzonitrile gave the above named compound. LCMS m/e [M+H]$^+$=323.

Example 31

Preparation of 2-(2-Fluoro-phenylamino)-7-methoxy-quinoline-3-carboxylic acid

Following the procedure of Example 13, with 2-fluoroaniline-in place of 3-aminobenzonitrile gave the above named compound. LCMS m/e [M+H]$^+$=313.

Example 32

Preparation of 2-(4-Ethoxy-2-fluoro-phenylamino)-7-methoxy-quinoline-3-carboxylic acid Following the procedure of Example 13, with 2-fluoro-3-ethoxyaniline-in place of 3-aminobenzonitrile gave the above named compound. LCMS m/e [M+H]$^+$=357.

Example 33

Preparation of 7-Methoxy-2-piperidin-1-yl-quinoline-3-carboxylic acid

Following the procedure of Example 1(a)–(c) except using DMSO as the solvent and piperidine in step (c), the title compound was prepared. LCMS m/e [M+H]$^+$=287.2.

Example 34

Preparation of 2-Propylamino7-methoxy-quinoline-3-carboxylic acid

Following the procedure of Example 1(a)–(c) except using DMSO as the solvent and propylamine in step (c), the title compound was prepared. LCMS m/e [M+H]$^+$=261.0.

Example 35

Preparation of 2-(3-Chloroanilino)--7-ethoxy-quinoline-3-carboxylic acid (a) 2-Chloro-3-formyl-7-ethoxy-quinoline
Using the method described in Example 1(a), the title compounds was prepared. LCMS m/e [M+H]$^+$=236.

(b) 2-Chloro-7-methoxy-quinoline-3-carboxylic acid
Using the method described in Example 1(b), the title compounds was prepared. ESMS m/e [M+H]$^+$=253.

(c) 2-(3-Chloroanilino)-7-ethoxy-quinoline-3-carboxylic acid
Following the procedure of Example 13, with 2-chloro-7-methoxy-quinoline-3-carboxylic acid from 35b and 3-chloroaniline-in place of 3-aminobenzonitrile gave the above named compound LCMS m/e [M+H]$^+$=343.

Example 36

Preparation of 2-Methyl 7-methoxy-quinoline-3-carboxylic acid (a) 2-Methyl-7-methoxy-2quinoline-3-carboxylic acid ethyl ester The title compound was prepared using the method outlined in Synthetic Communications 1987, 17 (14), 1647–1653. LCMS m/e [M+H]$^+$=246.2.

(b) 2-Methyl 7-methoxy-quinoline-3-carboxylic acid The material from above (2 g) was dissolved in ethanol and was treated with 9 mL 1N NaOH (aq). The reaction stirred at rt for 12 h. The reaction was evaporated and suspended in CHCl$_3$. The product was precipitated out with 1N HCl (aq). LCMS m/e [M+H]$^+$=218.2.

Example 37

Preparation of 2,7-Dimethyl-quinoline-3-carboxylic acid

Following the procedure of Example 36 (a)-(b) substituting m-toluidine in step 36 (a) gave the above named compound. LCMS m/e [M+H]$^+$=202.0.

Example 38

Preparation of 7-Methoxy-2-phenyl-quinoline-3-carboxylic acid

Following the procedure of Example 36 (a)-(b) substituting ethylbenzoylacetate in step 36 (a) gave the above named compound. LCMS m/e [M+H]$^+$=280.2

The above specification and Examples fully disclose how to make and use the compounds of the present invention. However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

The invention claimed is:

1. A compound of Formula I:

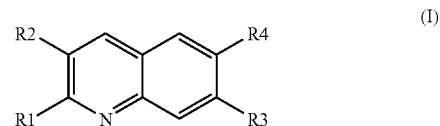

wherein:
$R_1$ is selected from the group consisting of: —NH—C$_{1-6}$ alkyl, —NH—C$_{3-7}$ cycloalkyl, —NH—C$_{3-7}$ cycloheteroalkyl, —NH-aryl, —NH-Het, —O—C$_{1-6}$alkyl, —O—C$_{3-7}$ cycloalkyl, —O—C$_{3-7}$ cycloheteroalkyl, —O-aryl, —O-Het, —S—C$_{1-6}$ alkyl, —S—C$_{3-7}$ cycloalkyl, —S—C$_{3-7}$ cycloheteroalkyl, —S-aryl, —S-Het, —C$_{3-7}$ cycloalkyl and —C$_{3-7}$ cycloheteroalkyl;

$R_2$ is selected from the group consisting of: —CO$_2$H, —CONH$_2$, and —CO$_2$R';

$R_3$ is selected from the group consisting of: —H, —OH, —C$_{1-6}$alkyl, —C$_{3-7}$ cycloalkyl, aryl, Het, —O—C$_{1-6}$ alkyl, —O—C$_{3-7}$ cycloalkyl, —O-aryl, —O-Het, —S—C$_{1-6}$alkyl, —S—C$_{3-7}$ cycloalkyl, —S-aryl, —S-Het, —NH—C$_{1-6}$alkyl, —NH—C$_{3-7}$ cycloalkyl, —NH-aryl, —NH-Het and halogen;

$R_4$ is selected from the group consisting of: —H, —C$_{1-6}$ alkyl, —C$_{3-7}$ cycloalkyl, aryl, Het, —O—C$_{1-6}$alkyl, —O—C$_{3-7}$ cycloalkyl, —O-aryl, —O-Het, —S—C$_{1-6}$ alkyl, —S—C$_{3-7}$ cycloalkyl, —S,-aryl, —S-Het, —NH—C$_{1-6}$alkyl, —NH—C$_{3-7}$ cycloalkyl, —NH-aryl, —NH-Het and halogen;

$R_3$ and $R_4$ can form a 5 to 7 membered ring comprising 0–3 heteroatoms independently selected from the group consisting of: O, N, and S;

$R_5$ is selected from the group —H and halogen;

R' is selected from the group consisting of: —C$_{1-6}$alkyl, —C$_{3-7}$cycloalkyl, and —C$_{3-7}$cycloheteroalkyl; and R" is selected from the group consisting of: —C$_{1-6}$alkyl, —C$_{3-7}$cycloalkyl, —C$_{3-7}$cycloheteroalkyl, aryl, and Het;

or a pharmaceutically acceptable salt, hydrate or solvate thereof.

2. A compound according to claim 1 wherein:
$R_1$ is selected from the group consisting of: —NH—C$_{1-6}$ alkyl, —NH-aryl, —NH-Het, —O-aryl, —O-Het, —S-aryl, —S-Het, and —C$_{3-7}$ cycloheteroalkyl, $R_3$ is selected from the group consisting of: —H, —C$_{1-6}$ alkyl, —O—C$_{1-6}$alkyl, —S—C$_{1-6}$alkyl, and halogen; and $R_4$ is —O—C$_{1-6}$alkyl, —S—C$_{1-6}$alkyl, and halogen.

3. A compound according to claim 2 wherein, when $R_2$ is —CO$_2$R, R' is selected from the group consisting of: —C$_{1-6}$ alkyl and —C$_{3-7}$cycloalkyl.

4. A compound according to claim 2 wherein:
$R_1$ is selected from the group consisting of: —NH—C$_{1-6}$ alkyl, —NH-aryl, —NH-Het, and —C$_{3-7}$ cycloheteroalkyl;

R$_2$ is selected from the group consisting of: —CO$_2$H and —CONH$_2$;

R$_3$ is selected from the group consisting of: —H, —C$_{1-6}$alkyl, —O—C$_{1-6}$alkyl, —S—C$_{1-6}$alkyl, and halogen; and R$_4$ is selected from the group consisting of: —H and halogen; and R$_5$ is —H.

5. A compound according to claim 4 wherein R$_4$ is H.

6. A compound according to claim 4 wherein:
- —NH-aryl is selected from the group consisting of: 3-methylphenylamino, 3-ethylphenylamino, 4-ethylphenylamino, 4-cyclohexylphenylamino, 3,4-dimethylphenylamino, 2-chlorophenylamino, 3-chlorophenylamino, 4-chlorophenylamino, 2-fluorophenylamino, 4-fluorophenylamino;, 4-iodophenylamino, 4-chlorobenzylamino, 4-morpholin-4-yl-phenylamino, 3-cyanophenylamino, 4-cyanophenylamino, 4-ethoxyphenylamino, 3,4-dimethoxyphenylamino, 4-phenoxyphenylamino and 2-fluoro-3-ethoxyphenylamino;
- —NH-Het selected from the group consisting of: quinolin-3-ylamino, quinolin-5-ylamino, quinolin-8-ylamino, pyridin-3-ylamino and 6-methoxy-pyridin-3-ylamino;
- —C$_{3-7}$ cycloheteroalkyl is N-piperidino; and
- —NH—C$_{1-6}$alkyl is 2-propylamino; and in R$_3$:
- —C$_{1-6}$alkyl is selected from the group consisting of :methyl and ethyl;
- —O—C$_{1-6}$alkyl is methoxy;
- —S—C$_{1-6}$alkyl is methylsulfanyl; and
- halogen is chloro.

7. A compound according to claim 6 wherein the compound of Formula I is selected from the group consisting of:
2-(3-chloroanilino)-3-carboxy-7-methoxy-quinoline;
2-(3-chloroanilino)-3-carboxy-7-chloro-quinoline; 2-(3-chloroanilino)-3-carboxy-7-methylthio-quinoline;
2-(4-chloroanilino)-3-carboxy-7-methoxy-quinoline;
2-(3-chloroanilino)-3-carboxamido-7-methoxy-quinoline;
2-(4-chlorobenzylamino)-3-carboxy-7-methoxy-quinoline;
2-(4-phenoxyanilino)-3-carboxy-7-methoxy-quinoline;
2-(4-morpholinanilino)-3-carboxy-7-methoxy-quinoline;
2-(3-chloroanilino)-3-carboxy-quinoline;
2-(3-chloroanilino)-3-carboxy-7-methyl-quinoline;
2-(3-chloroanilino)-3-carboxy-6-methoxy-quinoline;
2-(3-chloroanilino)-3-carboxy-7-ethyl-quinoline;
2-(3-cyanoanilino)-3-carboxy-7-methoxy-quinoline;
2-(3-methylanilino)-3-carboxy-7-methoxy-quinoline;
2-(4-ethoxyanilino)-3-carboxy-7-methoxy-quinoline;
2-(4-cyclohexylanilino)-3-carboxy-7-methoxy-quinoline;
2-(4-fluoroanilino)-3-carboxy-7-methoxy-quinoline;
2-(2-chloroanilino)-3-carboxy-7-methoxy-quinoline;
2-(4-ethylanilino)-3-carboxy-7-methoxy-quinoline;
2-(3-ethylanilino)-3-carboxy-7-methoxy-quinoline;
2-(4-cyanoanilino)-3-carboxy-7-methoxy-quinoline;
2-(3-aminoquinolino)-3-carboxy-7-methoxy-quinoline;
2-(4-iodoanilino)-3-carboxy-7-methoxy-quinoline;
2-(3-aminopyridino)-3-carboxy-7-methoxy-quinoline;
2-(5-amino-2-methoxypyridino)-3-carboxy-7-methoxy-quinoline;
2-(8-aminoquinolino)-3-carboxy-7-methoxy-quinoline;
2-(5-aminoquinolino)-3-carboxy-7-methoxy-quinoline;
2-(3,4-dimethoxyanilino)-3-carboxy-7-methoxy-quinoline;
2-(3,4-dimethylanilino)-3-carboxy-7-methoxy-quinoline;
2-(2-fluoroanilino)-3-carboxy-7-methoxy-quinoline;
2-(2-fluoro-3-ethoxyanilino)-3-carboxy-7-methoxy-quinoline;
2-piperidino-3-carboxy-7-methoxy-quinoline; and 2-propylamino-3-carboxy-7-methoxy-quinoline.

8. A compound according to claim 7 wherein the compound of Formula I is selected from the group consisting of:
2-(3-Chloro-phenylamino)-7-methoxy-quinoline-3-carboxylic acid;
7-Chloro-2-(3-chloro-phenylamino)-quinoline-3-carboxylic acid; 2-(3-Chloro-phenylamino)-7-methylsulfanyl-quinoline-3-carboxylic acid;
2-(4-Chloro-phenylamino)-7-methoxy-quinoline-3-carboxylic acid;
2-(4-Chloro-benzylamino)-7-methoxy-quinoline-3-carboxylic acid;
7-Methoxy-2-(4-phenoxy-phenylamino)-quinoline-3-carboxylic acid;
2-(3-Cyano-phenylamino)-7-methoxy-quinoline-3-carboxylic acid;
7-Methoxy-2-m-tolylamino-quinoline-3-carboxylic acid;
2-(4-Ethoxy-phenylamino)-7-methoxy-quinoline-3-carboxylic acid
2-(4-Cyclohexyl-phenylamino)-7-methoxy-quinoline-3-carboxylic acid;
2-(4-Fluoro-phenylamino)-7-methoxy-quinoline-3-carboxylic acid;
2-(2-Chloro-phenylamino)-7-methoxy-quinoline-3-carboxylic acid;
2-(4-Ethyl-phenylamino)-7-methoxy-quinoline-3-carboxylic acid;
2-(3-Ethyl-phenylamino)-7-methoxy-quinoline-3-carboxylic acid;
2-(4-Cyano-phenylamino)-7-methoxy-quinoline-3-carboxylic acid;
7-Methoxy-2-(quinolin-3-ylamino)-quinoline-3-carboxylic acid;
2-(4-Iodo-phenylamino)-7-methoxy-quinoline-3-carboxylic acid;
7-Methoxy-2-(6-methoxy-pyridin-3-ylamino)-quinoline-3-carboxylic acid;
7-Methoxy-2-(quinolin-8-ylamino)-quinoline-3-carboxylic acid;
7-Methoxy-2-(quinolin-5-ylamino)-quinoline-3-carboxylic acid;
2-(3,4-Dimethoxy-phenylamino)-7-methoxy-quinoline-3-carboxylic acid;
2-(2-Fluoro-phenylamino)-7-methoxy-quinoline-3-carboxylic acid; and
2-(4-Ethoxy-2-fluoro-phenylamino)-7-methoxy-quinoline-3-carboxylic acid.

9. A compound according to claim 8 wherein the compound of Formula I is selected from the group consisting of:
2-(3-Chloro-phenylamino)-7-methoxy-quinoline-3-carboxylic acid;
2-(3-Chloro-phenylamino)-7-methylsulfanyl-quinoline-3-carboxylic acid;
2-(4-Chloro-phenylamino)-7-methoxy-quinoline-3-carboxylic acid;
2-(3-Cyano-phenylamino)-7-methoxy-quinoline-3-carboxylic acid;
7-Methoxy-2-m-tolylamino-quinoline-3-carboxylic acid;
2-(4-Ethoxy-phenylamino)-7-methoxy-quinoline-3-carboxylic acid;
2-(4-Fluoro-phenylamino)-7-methoxy-quinoline-3-carboxylic acid;

2-(2-Chloro-phenylamino)-7-methoxy-quinoline-3-carboxylic acid;
2-(4-Ethyl-phenylamino)-7-methoxy-quinoline-3-carboxylic acid;
2-(3-Ethyl-phenylamino)-7-methoxy-quinoline-3-carboxylic acid;
2-(4-Cyano-phenylamino)-7-methoxy-quinoline-3-carboxylic acid;
2-(4-Iodo-phenylamino)-7-methoxy-quinoline-3-carboxylic acid;
7-Methoxy-2-(quinolin-8-ylamino)-quinoline-3-carboxylic acid;
7-Methoxy-2-(quinolin-5-ylamino)-quinoline-3-carboxylic acid;
2-(2-Fluoro-phenylamino)-7-methoxy-quinoline-3-carboxylic acid; and
2-(4-Ethoxy-2-fluoro-phenylamino)-7-methoxy-quinoline-3-carboxylic acid.

* * * * *

UNITED STATES PATENT AND TRADEMARK OFFICE
CERTIFICATE OF CORRECTION

PATENT NO. : 7,087,758 B2  Page 1 of 1
APPLICATION NO. : 10/474084
DATED : August 8, 2006
INVENTOR(S) : Bryan et al.

It is certified that error appears in the above-identified patent and that said Letters Patent is hereby corrected as shown below:

<u>On the Title page</u>: Title

Item (54) should read as follows:

-- (54)   QUINOLINE INHIBITORS OF HYAK1 AND HYAK3 KINASES --

Claim 1 (Column 28, Line 38) should read as follows:

-- alkyl, -S-$C_{3-7}$ cycloalkyl, -S-aryl, -S-Het, --

Claim 2 (Column 28, Line 55) should read as follows:

-- aryl, -S-Het, and -$C_{3-7}$ cycloheteroalkyl; --

Claim 6, (Column 29, Line 22) should read as follows:

-- -NH-Het is selected from the group consisting of: quino- --

Claim 8 (Column 30, Line 7) should read as follows:

-- 8. A compound according to claim 1 wherein the com- --

Signed and Sealed this

Twenty-fourth Day of June, 2008

JON W. DUDAS
*Director of the United States Patent and Trademark Office*

UNITED STATES PATENT AND TRADEMARK OFFICE
CERTIFICATE OF CORRECTION

PATENT NO. : 7,087,758 B2  Page 1 of 1
APPLICATION NO. : 10/474084
DATED : August 8, 2006
INVENTOR(S) : Bryan et al.

It is certified that error appears in the above-identified patent and that said Letters Patent is hereby corrected as shown below:

On the Title page: Title

Item (54) and Column 1, lines 1 and 2 should read as follows:

-- (54)   QUINOLINE INHIBITORS OF HYAK1 AND HYAK3 KINASES --

Claim 1 (Column 28, Line 38) should read as follows:

-- alkyl, -S-$C_{3-7}$ cycloalkyl, -S-aryl, -S-Het, --

Claim 2 (Column 28, Line 55) should read as follows:

-- aryl, -S-Het, and -$C_{3-7}$ cycloheteroalkyl; --

Claim 6, (Column 29, Line 22) should read as follows:

-- -NH-Het is selected from the group consisting of: quino- --

Claim 8 (Column 30, Line 7) should read as follows:

-- 8. A compound according to claim 1 wherein the com- --

This certificate supersedes the Certificate of Correction issued June 24, 2008.

Signed and Sealed this

Twenty-second Day of July, 2008

JON W. DUDAS
*Director of the United States Patent and Trademark Office*